(12) United States Patent
Tan et al.

(10) Patent No.: US 11,879,901 B2
(45) Date of Patent: Jan. 23, 2024

(54) CARTRIDGES FOR IMMUNOASSAY TESTS AND METHODS OF USING THE SAME

(71) Applicant: Access Medical Systems, LTD., Palo Alto, CA (US)

(72) Inventors: Hong Tan, San Jose, CA (US); Ming Xia, Shanghai (CN); Yushan Tan, Shanghai (CN); Jun Chen, Shanghai (CN); Erhua Cao, Shanghai (CN); Genqian Li, Shanghai (CN); Robert F. Zuk, Menlo Park, CA (US)

(73) Assignee: ACCESS MEDICAL SYSTEMS, LTD., Palo Alto, CA (US)

( * ) Notice: Subject to any disclaimer, the term of this patent is extended or adjusted under 35 U.S.C. 154(b) by 0 days.

(21) Appl. No.: 18/166,146

(22) Filed: Feb. 8, 2023

(65) Prior Publication Data

US 2023/0184792 A1   Jun. 15, 2023

Related U.S. Application Data

(60) Continuation of application No. 17/644,064, filed on Dec. 13, 2021, now Pat. No. 11,598,784, which is a
(Continued)

(51) Int. Cl.
*B65G 47/90* (2006.01)
*G01N 35/00* (2006.01)
(Continued)

(52) U.S. Cl.
CPC ............. *G01N 35/00* (2013.01); *B01L 3/527* (2013.01); *G01N 33/54353* (2013.01);
(Continued)

(58) Field of Classification Search
CPC .. G01N 35/00; G01N 33/54366; B01L 3/527; B01N 33/54353
(Continued)

(56) References Cited

U.S. PATENT DOCUMENTS 1,499,989 A   7/1924  Franz
2,754,708 A   7/1956  Peterson
(Continued)

FOREIGN PATENT DOCUMENTS

CN       2473613 Y      1/2002
CN     102358988 A      2/2012
(Continued)

*Primary Examiner* — Paul T Chin
(74) *Attorney, Agent, or Firm* — Perkins Coie LLP; Viola T. Kung; Andrew T. Pettit

(57) ABSTRACT

This invention relates to an apparatus for conducting immunoassay test. The apparatus includes a groove unit having a groove along a vertical direction configured to hold a rod-shaped portion of a probe along the vertical direction, and a push pin configured to move along a horizontal direction, the push pin being capable of residing at a first position and a second position. A tip of the push pin is capable of pressing the rod-shaped portion of the probe against the groove when the push pin resides at the first position. The distance between the tip of the push pin and the groove is larger than a diameter of the rod-shaped portion of the probe when the push pin resides at the second position.

18 Claims, 20 Drawing Sheets

Related U.S. Application Data continuation of application No. 16/421,015, filed on May 23, 2019, now Pat. No. 11,199,555, which is a continuation of application No. 15/784,966, filed on Oct. 16, 2017, now Pat. No. 10,345,319, which is a continuation of application No. 15/293,173, filed on Oct. 13, 2016, now Pat. No. 9,804,179, which is a continuation-in-part of application No. 14/301,228, filed on Jun. 10, 2014, now Pat. No. 9,468,926, which is a division of application No. 13/936,047, filed on Jul. 5, 2013, now Pat. No. 8,753,574, which is a continuation of application No. PCT/US2012/020532, filed on Jan. 6, 2012.

(60) Provisional application No. 61/430,963, filed on Jan. 8, 2011.

(51) Int. Cl.
*B01L 3/00* (2006.01)
*G01N 33/543* (2006.01)
*G01N 35/02* (2006.01)
*G01N 35/04* (2006.01)

(52) U.S. Cl.
CPC ........ *G01N 33/54366* (2013.01); *B01L 3/502* (2013.01); *B01L 2200/16* (2013.01); *B01L 2300/042* (2013.01); *B01L 2300/045* (2013.01); *G01N 35/026* (2013.01); *G01N 2035/0436* (2013.01)

(58) Field of Classification Search
USPC ................................. 294/87.1, 86.4
See application file for complete search history.

(56) References Cited

U.S. PATENT DOCUMENTS

| | | | |
|---|---|---|---|
| 3,796,239 A | 3/1974 | Zindler et al. | |
| 4,447,546 A | 5/1984 | Hirschfeld | |
| 4,572,564 A | 2/1986 | Cipolla | |
| 4,631,815 A | 12/1986 | Bocchicchio et al. | |
| 4,891,321 A | 1/1990 | Hubscher | |
| 5,011,207 A | 4/1991 | Stevens | |
| 5,605,665 A * | 2/1997 | Clark | G01N 21/03 422/63 |
| 5,637,275 A | 6/1997 | Carey et al. | |
| 5,650,334 A | 7/1997 | Zuk et al. | |
| 5,700,429 A | 12/1997 | Buhler et al. | |
| 5,884,906 A | 3/1999 | Morse | |
| 6,040,192 A | 3/2000 | Tuunanen | |
| 6,345,816 B1 | 2/2002 | Fitzpatrick | |
| 6,376,210 B1 | 4/2002 | Yuan et al. | |
| 6,464,939 B1 | 10/2002 | Bachand et al. | |
| 7,808,641 B2 | 10/2010 | Salerno et al. | |
| 7,811,829 B2 | 10/2010 | Kikuchi et al. | |
| 7,880,893 B2 | 2/2011 | Ghislain | |
| D669,597 S | 10/2012 | Cavada et al. | |
| D675,338 S | 1/2013 | Suzuki et al. | |
| 8,534,728 B1 | 9/2013 | Summer et al. | |
| D759,268 S | 6/2016 | Tan et al. | |
| 2003/0113235 A1 | 6/2003 | Yokoi et al. | |
| 2003/0153011 A1 | 8/2003 | Bell | |
| 2004/0161368 A1 | 8/2004 | Holtlund et al. | |
| 2005/0091839 A1 | 5/2005 | Xia et al. | |
| 2005/0266570 A1 | 12/2005 | Carey et al. | |
| 2006/0183217 A1 | 8/2006 | Yanagida et al. | |
| 2006/0216208 A1 | 9/2006 | Li et al. | |
| 2007/0116600 A1 | 5/2007 | Kochar et al. | |
| 2009/0260456 A1 | 10/2009 | Degli Esposti et al. | |
| 2010/0021890 A1 | 1/2010 | Schallmeiner | |
| 2013/0052081 A1 | 2/2013 | Tan et al. | |
| 2013/0295591 A1 | 11/2013 | Tan et al. | |
| 2014/0206088 A1 | 7/2014 | Lentz et al. | |
| 2016/0214114 A1 | 7/2016 | Tan et al. | |

FOREIGN PATENT DOCUMENTS

| | | |
|---|---|---|
| CN | 103753242 A | 4/2014 |
| EP | 1291654 A1 | 8/2003 |
| JP | 59175976 A | 10/1984 |
| JP | 3117587 U | 7/2005 |
| WO | 1994018564 A1 | 8/1994 |
| WO | 02090995 A2 | 11/2002 |
| WO | 2007084454 A2 | 7/2007 |
| WO | 2010101931 A2 | 9/2010 |

* cited by examiner

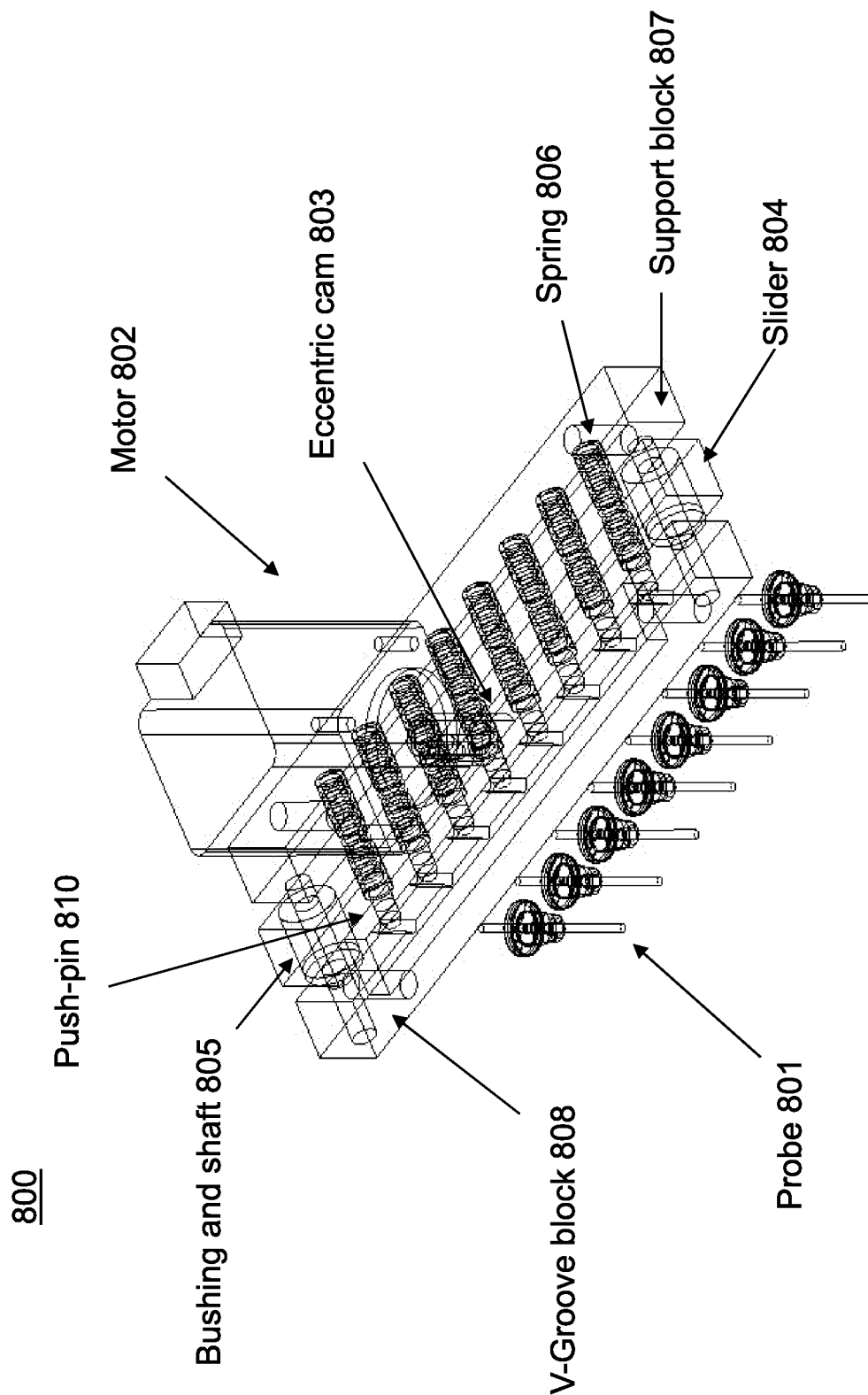

CARTRIDGES FOR IMMUNOASSAY TESTS AND METHODS OF USING THE SAME

This application is a continuation of U.S. application Ser. No. 17/644,064, filed Dec. 13, 2021; which is a continuation of U.S. application Ser. No. 16/421,015, filed May 23, 2019, now U.S. Pat. No. 11,199,555; which is a continuation of U.S. application Ser. No. 15/784,966, filed Oct. 16, 2017, now U.S. Pat. No. 10,345,319; which is a continuation of U.S. application Ser. No. 15/293,173, filed Oct. 13, 2016, now U.S. Pat. No. 9,804,179; which is a continuation-in-part of U.S. application Ser. No. 14/301,228, filed Jun. 10, 2014, now U.S. Pat. No. 9,468,926; which is a divisional of U.S. application Ser. No. 13/936,047, filed Jul. 5, 2013, now U.S. Pat. No. 8,753,574; which is a continuation of PCT/US2012/020532, filed Jan. 6, 2012; which claims the benefit of U.S. Provisional Application No. 61/430,963, filed Jan. 8, 2011. The contents of the above-identified applications are incorporated herein by reference in their entireties.

FIELD OF THE INVENTION

This invention relates to a system for conducting automated immunoassay tests. The system comprises a load and release mechanism to sequentially locate one or more probes to a plurality of wells on one or more cartridges. The invention also relates to a cartridge that comprises sample well, reagent well, wash wells, measurement well and a probe well to accommodate and secure the probe.

BACKGROUND OF THE INVENTION

In the development of immunoassay systems, many performance requirements need be met. Assays need be sensitive enough to detect analyte at very low levels in the subpicogram to nanogram per milliliter range. Total assay time needs to be 15 minutes or less in order to provide timely results for patient management in point of care situations, or to meet throughput requirements for batch analyzers. In some cases, analyte panels where multiple assays are simultaneously performed with the same sample are advantageous in order to minimize the turnaround time for results and test costs. All-in-one reagent cartridge and an automatic system conducting an immunoassay test on the cartridge is desired for minimal human input error, cost saving, and prompt results.

Many immunoassays employ fluorescent labels because such labels offer many practical advantages. Compared to enzymes, fluorescent labels are much more stable and do not require an additional substrate reagent. For multianalyte panels, fluorescent labels enable the use of discrete binding zones within a common reaction chamber since each binding zone can be sequentially subjected to fluorescence excitation and emission measurements without interference from adjacent binding zones. Assays utilizing fluorescent labels, however, are sometimes less sensitive than enzyme based assays primarily due to the enzyme's ability to catalytically convert substrate to accumulate a great amount of product molecules over time. Arylsulfonate cyanine fluorescent dyes are described in Mujumdar et al. (1993) *Bioconjugate Chemistry,* 4:105-111; Southwick et al. (1990) *Cytometry,* 11:418-430; and U.S. Pat. No. 5,268,486. Cy5 is described in each of the references and is commercially available from Biological Detection Systems, Inc., Pittsburgh, Pa., under the tradename FLUOROLINK™ Cy5™. The arylsulfonate cyanine fluorescent dyes have high extinction coefficients (typically from 130,000 L/mole to 250,000 L/mole), good quantum yields, fluorescent emission spectra in a range (500 nm to 750 nm) outside of the autofluorescence wavelengths of most biological materials and plastics, good solubilities, and low non-specific binding characteristics.

There exists a need for immunoassay apparatuses and disposables, which are sensitive for detection of analytes and can be used in an automated system.

SUMMARY OF THE INVENTION

The present invention is directed to a cartridge for an immunoassay test. The cartridge comprises (a) a probe well comprising a probe and a cap, the cap being in a closed position to enclose the probe in the probe well, wherein the probe has a bottom tip coated with analyte-binding molecules; (b) a sample well to receive a sample; (c) one or more reagent wells; (d) a plurality of wash wells each containing a first aqueous solution; and (e) a measurement well having a light transmissive bottom, the measurement well containing a second aqueous solution; wherein the openings of the sample well, reagent well, measurement well and wash wells are sealed.

The present invention is also directed to a probe. The probe is made to have (a) a rod having a bottom tip; (b) a flange surrounding the rod; and (c) a sleeve under the flange; wherein the bottom tip is coated with analyte-binding molecules and the rod has a portion extruding from a top side of the flange.

The present invention is also directed to an apparatus for loading and releasing at least one probe having a rod-shaped portion. The apparatus comprising (a) a groove unit having a groove along a vertical direction configured to hold the rod-shaped portion of the probe along the vertical direction; and (b) a push pin configured to move along a horizontal direction, the push pin being capable of residing at a first position and a second position; wherein a tip of the push pin is capable of pressing the rod-shaped portion of the probe against the groove when the push pin resides at the first position; and the distance between the tip of the push pin and the groove is larger than a diameter of the rod-shaped portion of the probe when the push pin resides at the second position.

The present invention is also directed to an apparatus for loading and releasing a plurality of probes, each probe of the plurality of probes having a rod-shaped portion having a common diameter. The apparatus comprises a plurality of pairs of groove unit and push pin. Each pair comprises (a) a groove unit having a groove along a vertical direction configured to hold the rod-shaped portion of the probe along the vertical direction; and (b) a push pin configured to move along a horizontal direction, the push pin being capable of residing at a first position and a second position; wherein the tip of the push pin is capable of pressing the rod-shaped portion of the probe against the groove when the push pin resides at the first position; the distance between the tip of the push pin and the groove is larger than the common diameter of the rod-shaped portion of the probe when the push pin resides at the second position; and the push pins of the pairs are mechanically coupled so that the push pins move along the horizontal direction simultaneously.

BRIEF DESCRIPTION OF THE DRAWINGS

FIG. 8 illustrates an example of an apparatus for loading and releasing a plurality of probes.

DETAILED DESCRIPTION OF THE INVENTION

Definitions

Figure 1:
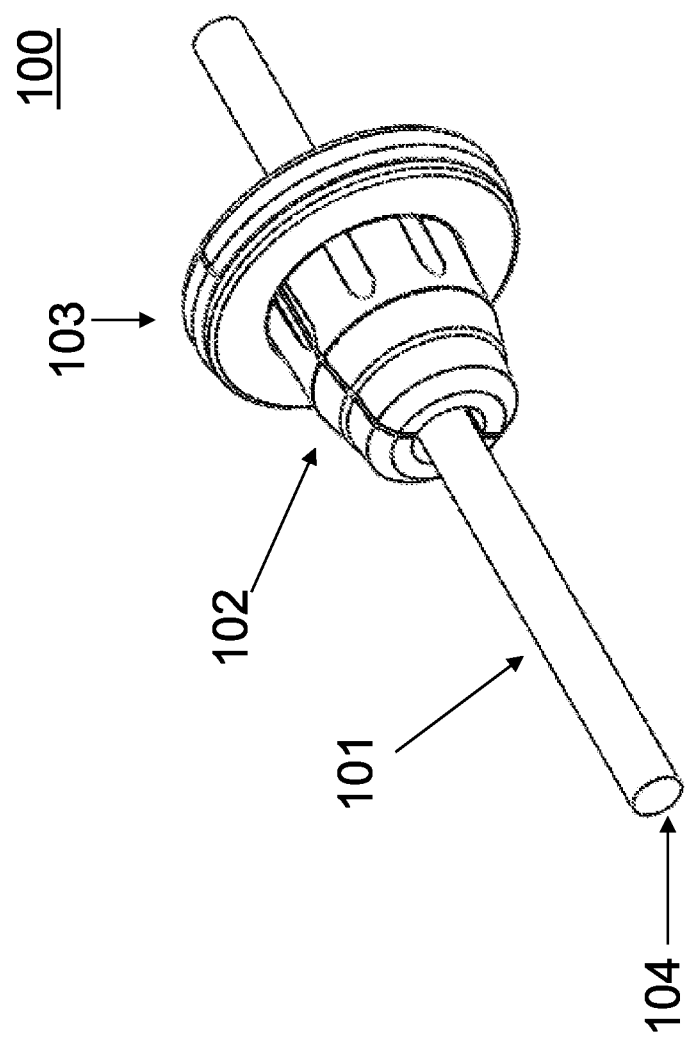
FIG. 1 illustrates an example of a probe to be used in an immunoassay test.

Terms used in the claims and specification are to be construed in accordance with their usual meaning as understood by one skilled in the art except and as defined as set forth below.

"About," as used herein, refers to within ±10% of the recited value.

An "analyte-binding" molecule, as used herein, refers to any molecule capable of participating in a specific binding reaction with an analyte molecule. Examples include but are not limited to, (i) antigen molecules, for use in detecting the presence of antibodies specific against that antigen; (ii) antibody molecules, for use in detecting the presence of antigens; (iii) protein molecules, for use in detecting the presence of a binding partner for that protein; (iv) ligands, for use in detecting the presence of a binding partner; or (v) single stranded nucleic acid molecules, for detecting the presence of nucleic acid binding molecules.

An "aspect ratio" of a shape refers to the ratio of its longer dimension to its shorter dimension.

A "binding molecular," refers to a molecule that is capable to bind another molecule of interest.

"A binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, lectin and carbohydrates. Preferred binding pairs are biotin and streptavidin, biotin and avidin, fluorescein and anti-fluorescein, digioxigenin/anti-digioxigenin. Biotin and avidin, including biotin derivatives and avidin derivatives such as streptavidin, may be used as intermediate binding substances in assay protocols employing complex binding sequences. For example, antibodies may be labeled with biotin ("biotinylated") and used to bind to a target substance previously immobilized on a solid phase surface. Fluorescent compositions according to the present invention employing an avidin or streptavidin may then be used to introduce the fluorescent label.

"Immobilized," as used herein, refers to reagents being fixed to a solid surface. When a reagent is immobilized to a solid surface, it is either be non-covalently bound or covalently bound to the surface.

A "probe," as used herein, refers to a substrate coated with analyte-binding molecules at the sensing (detecting) side. A probe has a bottom tip. The bottom tip has a sensing surface coated with analyte-binding molecules.

Immunoassay Cartridge and Probe

The present invention is directed to a cartridge for an immunoassay test. The cartridge comprises (a) a probe well comprising a probe and a cap, the cap being in a closed position to enclose the probe in the probe well, wherein the probe has a bottom tip coated with analyte-binding molecules; (b) a sample well to receive a sample; (c) one or more reagent wells; (d) a plurality of wash wells each containing a first aqueous solution; and (e) a measurement well having a light transmissive bottom, the measurement well containing a second aqueous solution; wherein the openings of the sample well, reagent well, measurement well and wash wells are sealed.

The probe can be a monolithic substrate, or include a monolithic substrate, or assembled with sub-components. For example, the probe can include a monolithic substrate; and a bottom tip of the probe or a bottom tip of the monolithic substrate can be coated with analyte-biding molecules. The cross section of the rod portion of the probe can be any shape such as round, square, triangle, etc. The rod portion has an aspect ratio of length to width of at least 5 to 1, preferably greater than 10 to 1. Because the probe is dipped in a sample solution and one or more assay solutions during an immunoassay, it is desirable to have a long probe with an aspect ratio of at least 5 to 1 to enable the probe tip's immersion into the solutions. Heterogeneous assays can be performed where the long probe is transferred to different reaction and wash chambers or wells. The sensing surface of the probe is coated with analyte-binding molecules and bound with fluorescent labels.

The bottom tip of the probe is coated with analyte-binding molecules. Analyte-binding molecules, for example, are antigen molecules, antibody molecules, protein molecules, or ligands. Preferably, the probe is coated with a first antibody that binds to the analyte. Methods to immobilize molecules to a solid phase (the bottom tip of the probe) are common in immunochemistry and involve formation of covalent, hydrophobic or electrostatic bonds between the solid phase and molecules. Analyte-binding molecules can be directly immobilized on the surface of the tip. Alternatively, analyte-binding molecules can be indirectly immobilized on the surface of the tip through a binding pair. For example, anti-fluorescein can be first immobilized either by adsorption to the solid surface or by covalently binding to aminopropylsilane coated on the solid surface. Then the analyte-binding molecule that is labeled with fluorescein can be bound to the solid surface through the binding of fluorescein and anti-fluorescein (binding pair). In a preferred embodiment, the analyte-binding molecules are first antibody molecules that bind to the antigen analyte in a sample.

A sample well is a well that receives a sample containing an analyte. A sample well can be a blank well, or it can contain detergents, blocking agents and various additives for the immunoassay, either in a dry format or in a wet (liquid) format. In human blood samples, heterophile antibodies (antibodies that bind IgG from other species) and rheumatoid factor are common interfering substances for immunoassays. There are a variety of blocking agents minimizing this form of interference. For examples, blocking agents include IgGs from different species such as murine IgGs, heat aggregated IgG, crosslinked IgG, and commercially available heterophile blockers. The wet format typically contains a small liquid volume (<10 µL e.g., 5 µL). The dry format includes a lyophilization cake, powder, tablet or other formats typical in diagnostic kits; the dry format is to be reconstituted to a wet format by a reconstitution buffer and/or sample. The sample well serves as a primary reaction chamber for the reaction between the analyte in the sample and the analyte-binding molecules coated on the probe to form an immunocomplex.

The cartridge comprises one or multiple reagent wells. The reagent wells contain reagents that react with the immunocomplex and generate a signal for detection. The reagents can be in a wet format or in a dry format. The wet format contains a reagent in an assay buffer. The wet format is typically in a small liquid volume (<10 µL, e.g., 5 µL). An assay buffer typically includes a buffer (e.g., phosphate, tris), a carrier protein (e.g., bovine serum albumin, porcine serum albumin, and human serum albumin, 0.1-50 mg/mL), a salt (e.g., saline), and a detergent (e.g., Tween, Triton). An example of an assay buffer is phosphate buffered saline, pH 7.4, 5 mg/ml bovine serum albumin, 0.05% Tween 20. The assay buffer optionally contains a blocking agent in an amount of 1-500 µg/mL. The final formulation will vary depending on the requirements of each analyte assay. The dry format is the dry form of the reagent in an assay buffer. The dry format includes lyophilization cake, powder, tablet or other formats typical in diagnostic kits. The dry format is to be reconstituted to a wet format by a reconstitution buffer. In one embodiment, the cartridge contains only one reagent well. The reagent well contains an analyte-binding molecule labeled with a reporter molecule, wherein the analyte-binding molecule binds to the analyte molecule. For example, the analyte-binding molecule is a second antibody that binds to the analyte.

In a preferred embodiment, the cartridge contains two or more reagent wells. For example, a first reagent well contains second antibody molecules (that bind to the analyte) conjugated with a first member of a binding pair, and a second reagent well contains a second member of the binding pair labeled with reporters. For example, the first reagent well is a biotin reagent well containing a biotinylated second antibody directed against the analyte. The second reagent well is a streptavidin reagent well containing streptavidin labeled with reporters. The reporters can be any of those typically used in diagnostic kits, i.e. fluorescent, chemiluminescent, or enzyme labels.

The cartridge comprises multiple washing wells each containing an aqueous solution. The wash wells contain a wash buffer to wash the probe after binding steps in the sample well and reagent well(s). One to four wash wells (e.g., 1, 2, 3, or 4 wells) are dedicated for washing after each binding step. Wash buffers contain detergents. Any detergent typically used in immunoassays (e.g., Tween, Triton) can be used in this invention.

The cartridge comprises a measurement well having an optically clear bottom that enables the detection of the labeled-immunocomplex bound to the bottom tip of the probe. The measurement is through the bottom of the well. The measurement well contains a liquid solution. In the case when the label is an enzyme, the aqueous solution contains a substrate of the enzyme.

In one embodiment, some of the wash wells are served for the purpose of reconstituting the dry forms in the sample well and reagent well(s).

In another embodiment, the cartridge further comprises reconstitution wells that contain reconstitution buffer to be dispensed into the sample wells and reagent wells to reconstitute the dry forms in the sample well and reagent well(s). The reconstitution buffer can be simply a buffer such as phosphate-buffer saline. The reconstitution buffer can additionally include other additives (carrier protein, blockers, detergents, etc.) contained in the assay buffer. Several configuration of the reconstitution wells are feasible. For example, there can be several wells, each contains 50~200 µL, e.g. 100 µL of reconstitution buffer, and each dedicated to each one of the sample and reagents. Or there can be a single well with a sufficient volume for all the sample and reagents.

For reporter molecule that labels the immunocomplex, fluorescent labels are preferred. When the analyte-binding molecule is a protein, such as an antibody, the fluorescent label can covalently bind to it through a variety of moieties, including disulfide, hydroxyphenyl, amino, carboxyl, indole, or other functional groups, using conventional conjugation chemistry as described in the scientific and patent literature. Alternatively, antibodies can be biotinylated by known techniques (see Wilchek and Bayer, (1988) ANAL. BIOCHEM. 171:1-32) and linked to the fluorescent label via avidin/streptavidin molecules. Exemplary techniques for binding arylsulfonate cyanine fluorescent dye labels to antibodies and other proteins are described in U.S. Pat. Nos. 5,268,486; 5,650,334; the contents of which are in incorporated herein by reference. Techniques for linking a preferred Cy5 fluorescent label to antibodies acids are described in a technical bulletin identified as Cat. No. A25000, published by Biological Detection Systems, Inc., Pittsburgh, Pa. Cy5-streptavidine-crosslinked ficoll, disclosed in WO2010/101931, has multiple fluorescent labels in one molecule and can be used in the cartridge of the present invention to enhance the signal.

In addition to fluorescent labels, the cartridge of the present invention is compatible with many other commonly used labels for immunoassays such as enzymes (HRP or alkaline phosphatase) and chemiluminescence labels. Reagents with enzymes conjugated to either a second antibody or streptavidin can be used to bind the immunocomplex and its signal is readily detected through the clear bottom in the measurement well containing enzyme substrates. Multiple detection modes are possible depending on the optical properties of the enzyme product, such as reflectance or adsorption of colorimeteric products. The HRP/luminal system is the salient example of a chemiluminescent enzyme assay that is possible with the cartridge of the present invention.

Assays using chemiluminescent haptens such as ruthenium salts for electrochemiluminescent assays is compatible with the cartridge of the present invention. A reagents with ruthenium (II) tris (bispyridyl) labeled to either streptavidin or the second antibody can be used to bind the immunocomplex and its signal is detected in a measurement well containing tripropylamine in solution and a working and counter electrode pair. When the appropriate voltage is applied to the electrodes, the ruthenium salt and tripylamine react to generate light, which is detected through the clear bottom of the measurement well.

FIG. 1 illustrates an example of a probe 100 to be used in an immunoassay test. As shown in FIG. 1, the probe 100 comprises a rod section 101 (also referred to as rod-shaped center segment), a sleeve section 102 and a flange section 103. The flange 103 and the sleeve 102 surround the rod 101 and are located in the middle portion of the rod 101. The bottom tip 104 of the rod 101 may have been coated with immobilized analyte-binding molecules, such as antibody or antigen, on its detection surface.

The probe can be made as one piece by manufacturing processes such as molding, casting or machining. The probe can also be made from separate sub-components. The top portion of the rod may have a different size from the bottom portion. In this case, the rod can be made from, but not limited to, a segment of optical fiber, a glass rod, a metal rod, a plastic rod or a ceramic rod. The rod 101 may comprise different material than the sleeve 102.

Figure 2:
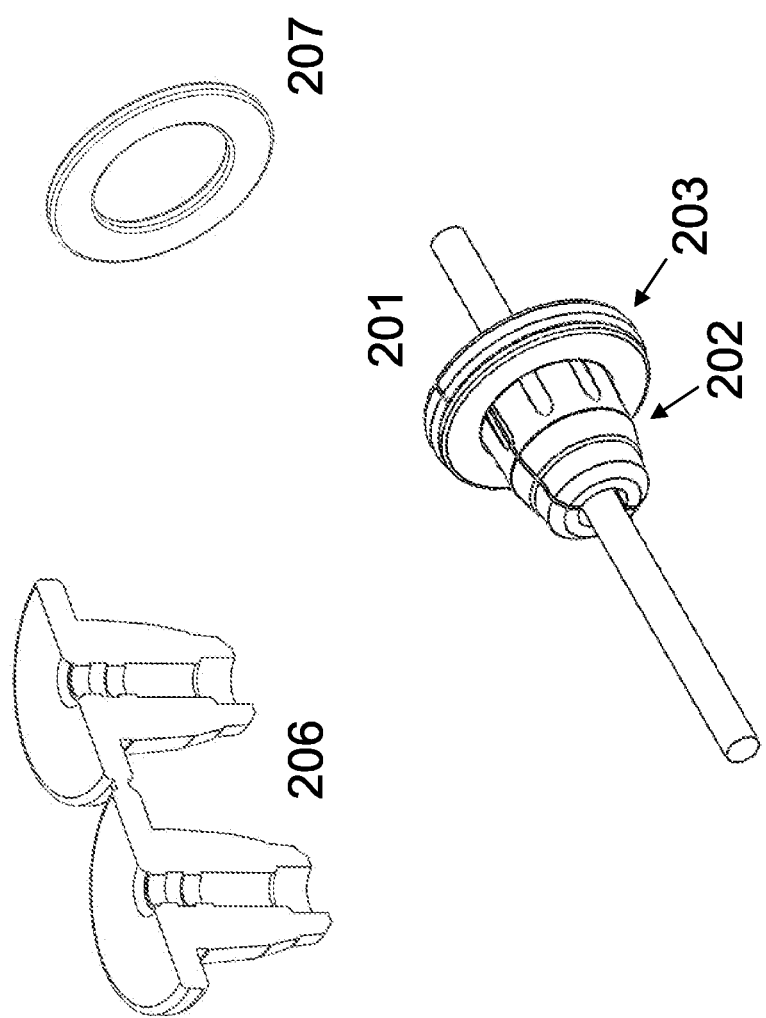
FIG. 2 illustrates components of a probe, according to one embodiment assembled using components.

FIG. 2 illustrates components of probe 100, according to one embodiment of the present invention. A plastic holder 206 can be closed and clip onto the rod 201 to form the sleeve 202 and part of the flange 203. A fastener ring 207 is disposed on the plastic holder 206 to secure the plastic holder 206 on the rod 201 and serves as part of the flange 203.

Figure 3:
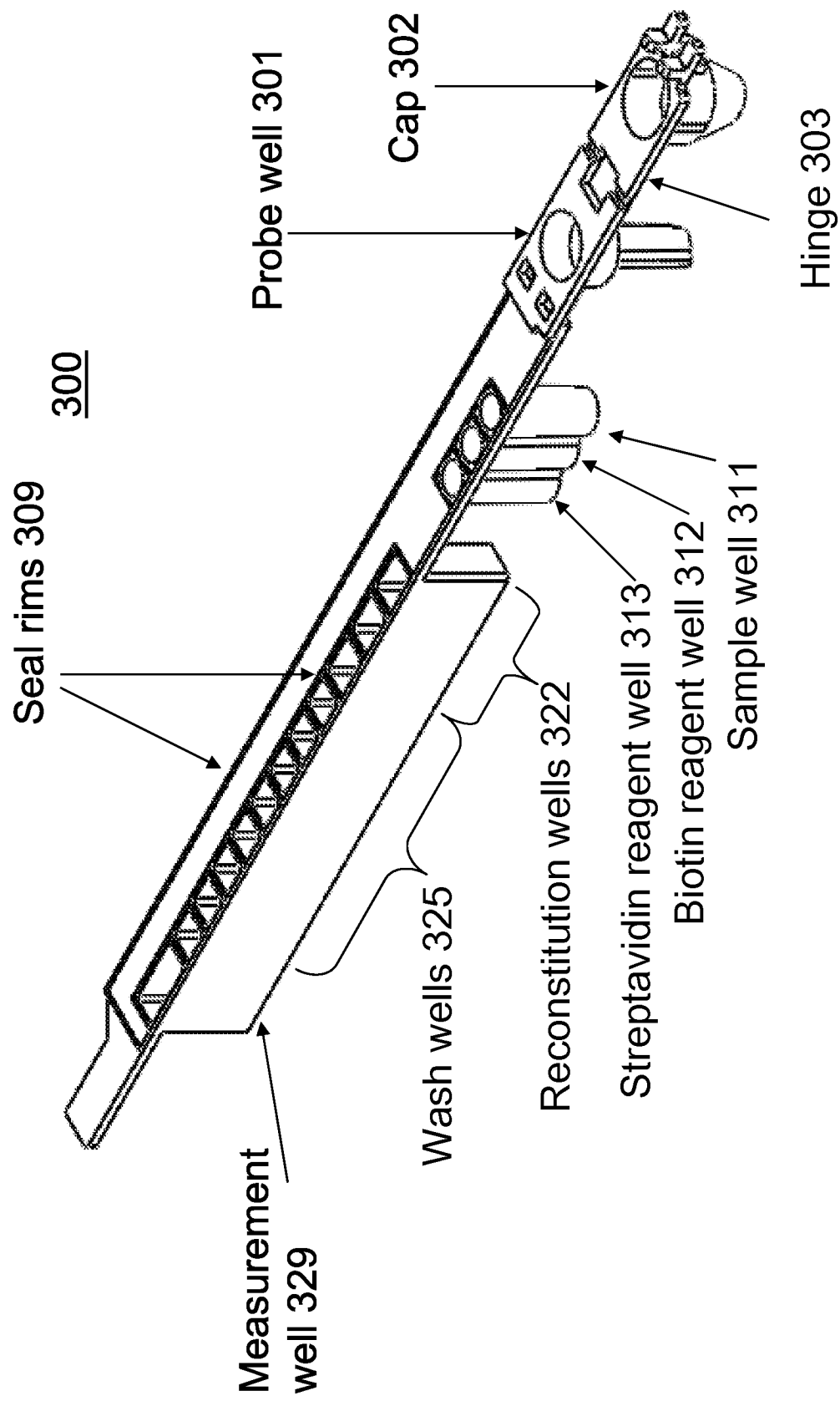
FIG. 3 illustrates an example of a cartridge.

FIG. 3 illustrates an example of the cartridge of the present invention. Cartridge 300 comprises a probe well 301 and a protective cap 302 to accommodate and secure the probe. The probe well 301 serves as a protective container for the probe. In one embodiment, the cap 302 is mechanically coupled to the probe well 301 via a hinge 303. After the probe is inserted in the probe well 301, the cap 302 is folded over the probe well 301 to fully enclose the probe. The probe may be vertically stored inside the probe well 301 when the protective cap 302 is in a closed position.

The cartridge 300 may comprise two separate compartments of wells. The first compartment comprises a sample well 311, biotin reagent well 312 and streptavidin reagent 313. The biotin reagent in the biotin reagent well 312 comprises a biotinylated second antibody. The streptavidin reagent well 313 contains a labeled streptavidin. The label may be any typical label used in diagnostic kits, such as fluorescent, chemiluminescent, or enzyme labels. The biotin and streptavidin reagents may be in dry format or in a wet format of about 5 μL liquid.

The second compartment comprises reconstitution wells 322, wash wells 325, and a measurement well 329. The reconstitution wells 322 contain a reconstitution buffer to be dispensed into the sample, the biotin reagent and the streptavidin reagent wells 311-313 for reconstituting the dry reagents in these wells. The liquids in reconstitution wells may be transferred to wells 311-313 using pipettes. Each of the wash wells 325 contains a first aqueous solution to wash the probe after binding steps in the sample, biotin reagent, and streptavidin reagent wells 311-313.

The measurement well 329 contains a second aqueous solution. In one embodiment, the second aqueous solution is the same as the first aqueous solution. The measurement well 329 has a light transmissive bottom, which may be transparent or translucent. The light transmissive bottom is used for an optical reading during the immunoassay test. The optical signal at the bottom tip of the probe is read through the light transmissive bottom. In one embodiment, a laser beam is projected through the light transmissive bottom to the bottom tip of the probe excite a fluorescent label; the fluorescent signal is collected through the light transmissive bottom. In some embodiment, the thickness of the light transmissive bottom is less than 1 mm. The first and second compartments are separate by an air space to prevent liquid penetration from wells containing liquids to wells containing dry reagents.

The technique of fluorescent signal detection in a measurement well is discussed in details in PCT Application No. WO2010/101931, the content of which is incorporated herein by reference in its entirety.

The openings of the wells is sealed with a foil or a film. The seal is penetrable. The wells may be opened by piercing the seal by a manual or automated device. To achieve better sealing, rims 309, i.e. small raised lines, are built around the opening of the wells and the edges round the wet and/or dry well areas.

In one embodiment, the cartridge is used to conduct an immunoassay test. Using a pipettor dispensing subsystem, about 20-100 μL (e.g. 50 μL) of the reconstitution buffer is transferred from reconstitution wells to each of the sample well, the biotin reagent well, and the streptavidin well on the cartridge. An aliquot of about 10-50 μL (e.g. 20 μL) of sample is transferred from a sample tube to the sample well by a pipettor. The cap of the probe well is opened and the probe is transferred to the sample well and the bottom tip of the probe is immersed in the liquid sample mixture. The probe incubates with the liquid sample mixture for a period of time. Afterward, the probe is sequentially transferred to one or more (e.g. 2-4) wash wells. Subsequently, the probe is transferred to a biotin reagent well and incubated for a period of time. The probe is sequentially transferred to wash wells. Afterward, the probe is transferred to a streptavidin reagent well and incubated for a period of time. The probe is sequentially transferred to wash wells and lastly transferred to a measurement well. The labeled streptavidin at the bottom tip of the probe is detected through a light transmissive window of the measurement well.

The present invention provides a method for conducting an automated immunoassay test using the cartridge. The method comprising (a) unlocking the cap of the probe well to an open position; (b) descending a push pin and a groove unit having a groove down in a vertical direction; (c) loading the probe between the push pin and the groove; (d) ascending the groove and the push pin; (e) shifting the groove and the push pin in a horizontal plane to a location on top of the sample well; (f) descending the groove and the push pin to dip the bottom tip of the probe into the sample well comprising a sample solution having an analyte without touching an inner surface of the sample well, and allowing a reaction between the analyte and the analyte-binding molecules coated on the bottom tip of the probe for a first period of time to form an immunocomplex; (g) ascending the groove and the push pin; (h) shifting the groove and the push pin in the horizontal plane to a location on top of the reagent well; (i) descending the groove and the push pin to dip the bottom tip of the probe into the reagent well without touching an inner surface of the reagent well, and allowing a reaction between the immunocomplex and the reagent for a second period of time; (j) ascending the groove and the push pin; (k) shifting the groove and the push pin in the horizontal plane to a location on top of a wash well; (l) descending the groove and the push pin to dip the bottom tip of the probe into said wash well without touching an inner surface of said wash well, and washing away non-specifically bound materials on the probe; (m) ascending the groove and the push pin; (n) shifting the groove and the push pin in the horizontal plane to a location on top of the measurement well; (o) descending the groove and the push pin to dip the bottom tip of the probe into the measurement well and maintaining the bottom tip of the probe in a distance from an inner surface of the measurement well; and (p) detecting the immunocomplex formed by detecting a optical signal on the bottom tip of the probe through the light transmissive bottom. The method may be automatically executed by the apparatus based on a pre-determined sequence.

Figure 4:
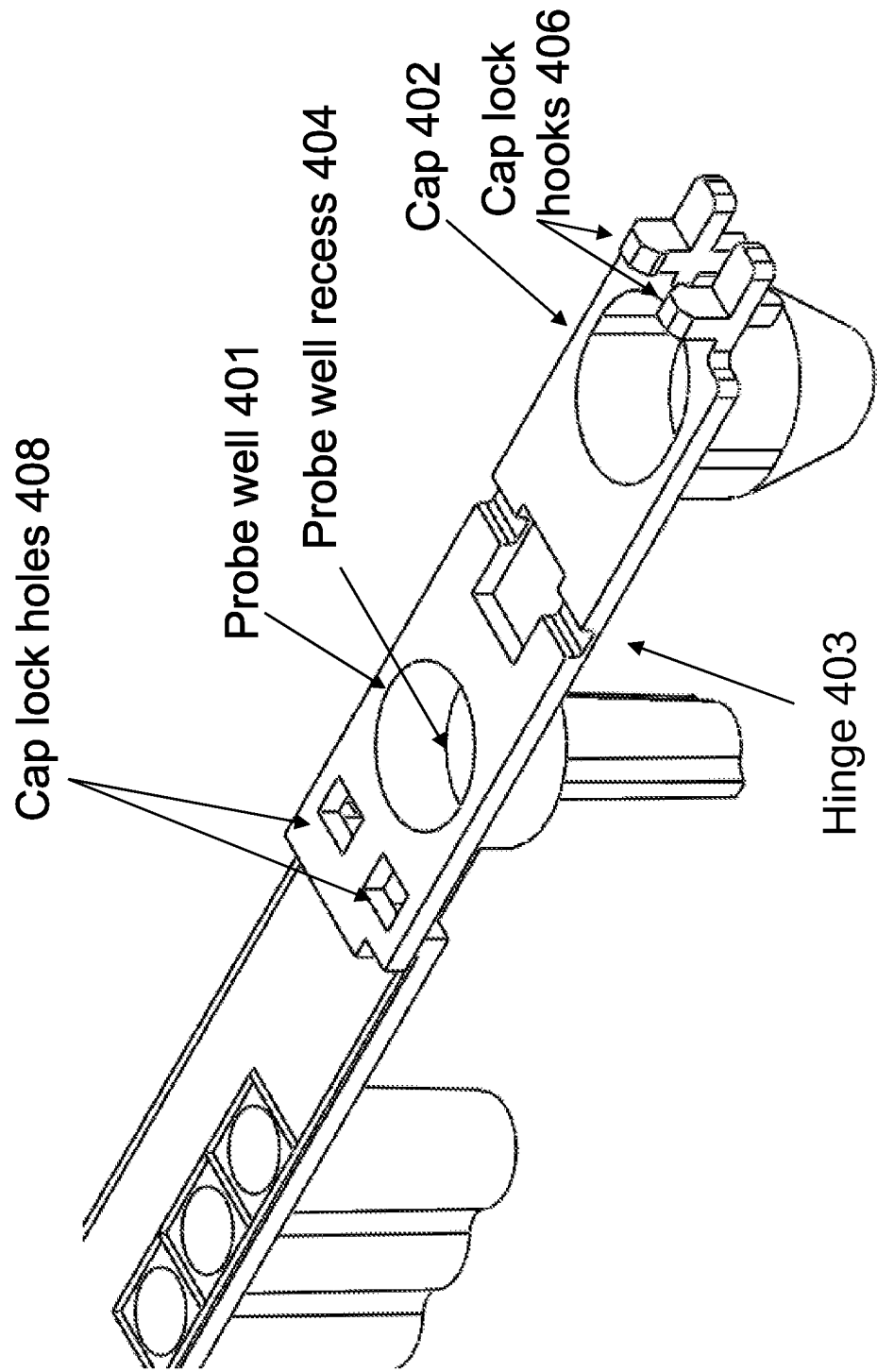
FIG. 4 illustrates an example of a probe well and a cap of a cartridge.

FIG. 4 illustrates an example of the probe well 401 and the cap 402 of the cartridge, according to one embodiment of the present invention. The cap 402 is hinged to the probe well 402 via a hinge 403 sot that the cap 402 can rotate to a closed position and an open position. The open position of the cap 402 is shown in the FIG. 4. The probe well 401 has a recess 404 inside of the opening of the probe well 401. A cushion may be placed on the recess 404 to support the probe when the probe is stored vertically. The cap 402 may have a pair of lock hooks 406; there are a corresponding pair of cap lock holes 408 near the probe well 401. In one embodiment, the lock hooks are small raised bumps on the fingers. An ordinary skilled person in the art will readily use other shapes or mechanisms to serve the purpose of the hook. When the cap 402 is in a closed position, the lock hooks 406 are inserted into the lock holes so that the cap 401 is locked in the closed position.

Figure 5A:
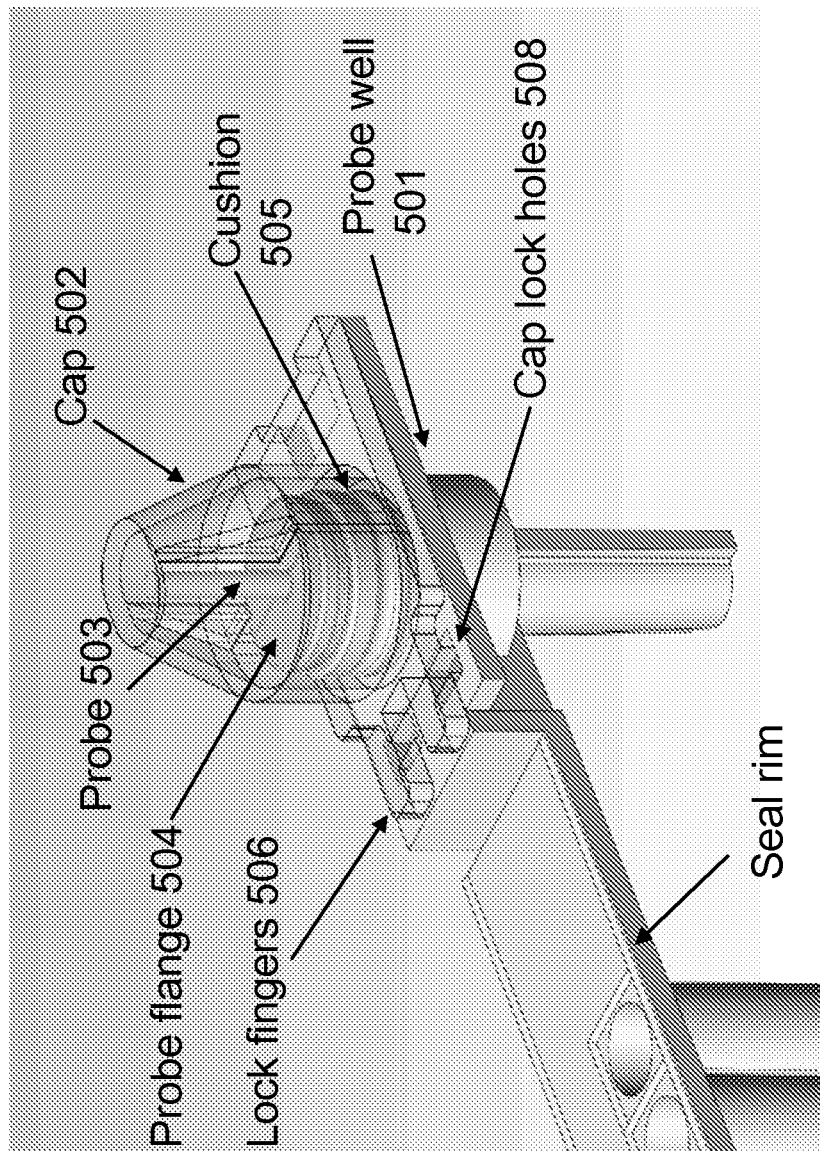
FIG. 5A illustrates an example of a probe well and a cap when the cap is in a closed position.

FIG. 5A illustrates an example of the probe well 501 and the cap 502 when the cap 502 is in a closed position, according to one embodiment of the present invention. In order to release the cap 502, the two lock fingers 506 need to be pushed outward slightly to disengage the hooks. The probe 503 is stored vertically inside the probe well. An elastic cushion 505 may be used to support the probe 503 on the flange 504. The elastic cushion 505 may be made from rubber, silicon, foam, spring, or other elastic materials. In one embodiment, the cushion 505 is O-ring shaped. In other embodiments, the cushion 505 may have other shapes such as square or polygon. In one embodiment, the cushion 505 may be disposed on the recess in the probe well 501, or attached to the recess in the probe well 501 by adhesive. In another embodiment, the cushion may be attached to the bottom of the flange 504. When the cap 502 is in the closed position, the cushion 505 secures the probe flange 504 so that the bottom tip of the probe maintains a distance from an inner surface of the probe well without touching the inner surface. When the probe 503 experiences a downward force during the automated immunoassay test, the cushion prevents the bottom tip of the probe form touching the inner surface of the probe well.

Figure 5B:
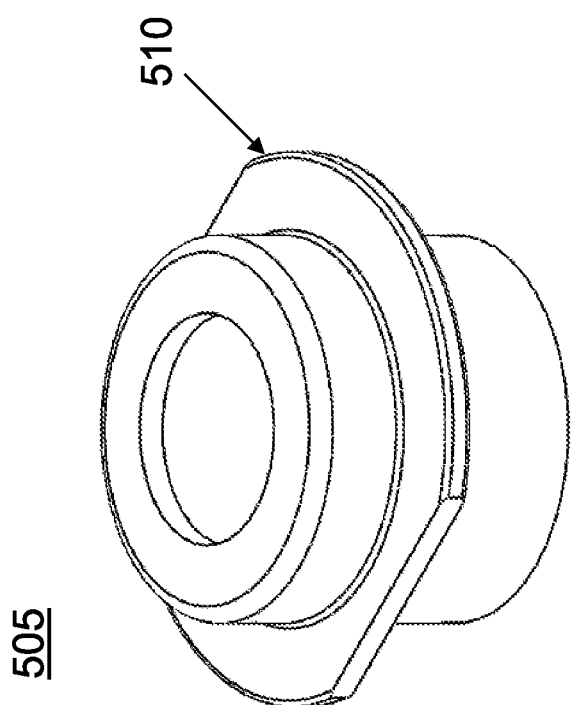
FIG. 5B illustrates an example of a cushion having a gasket ring portion.

In some embodiments, the cushion 505 may further have a gasket ring portion 510 as shown in FIG. 5B. When the cap is in the closed position, the gasket ring 510 fills in between the opening of the probe well 501 and the flange 504, so that the probe well forms an impermeable chamber enclosing the bottom tip of the probe, to prevent moisture from reaching the bottom tip.

Figure 6A:
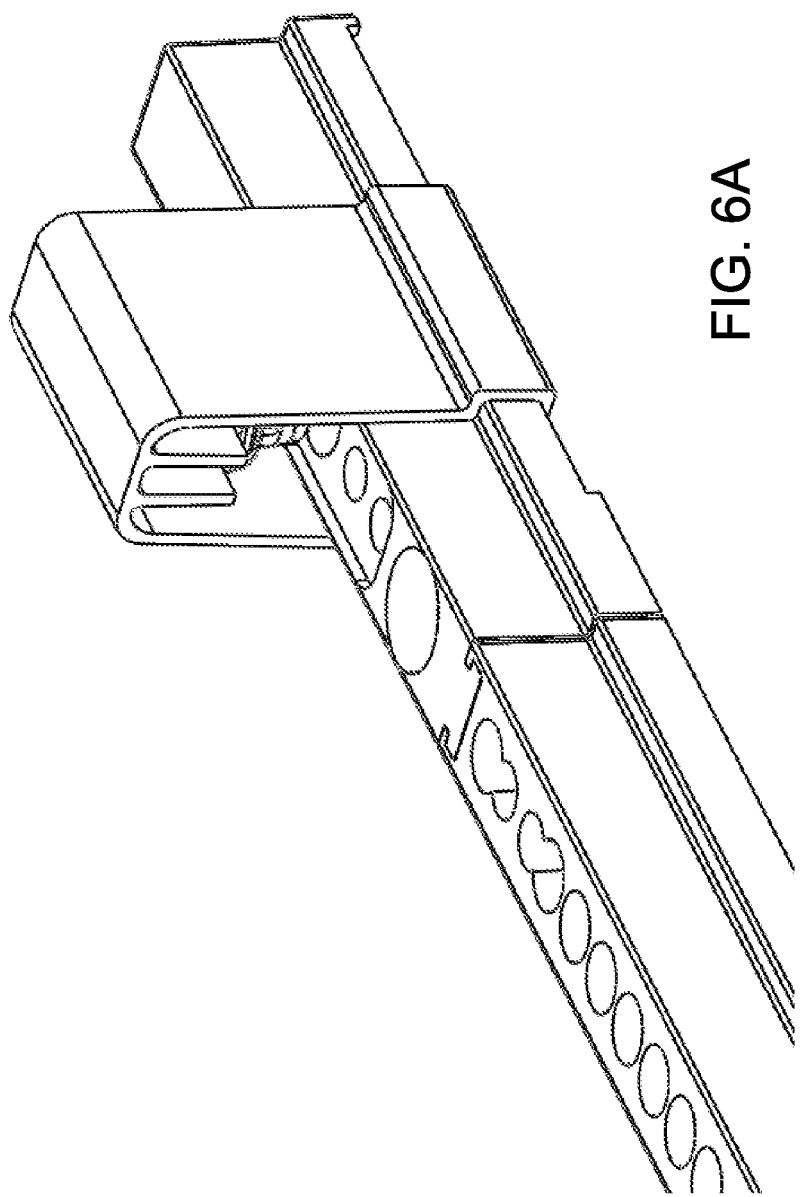
FIG. 6A illustrates an example of a probe well and a sliding cap in a close position.
Figure 6B:
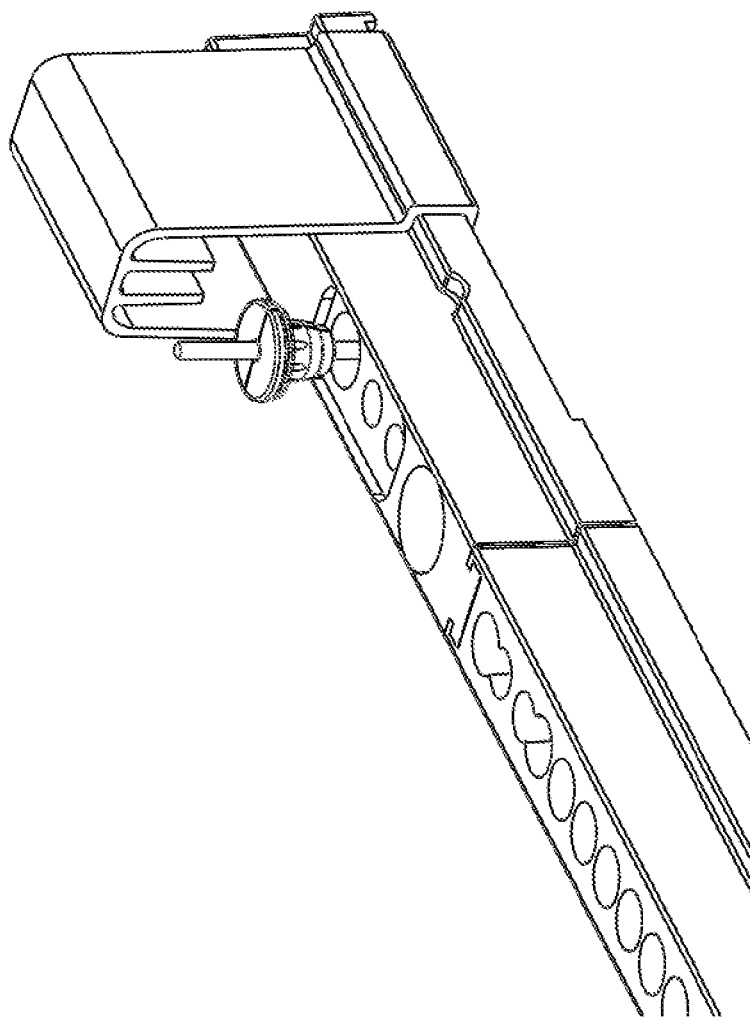
FIG. 6B illustrates an example of a probe well and a sliding cap in an open position.
Figure 7A:
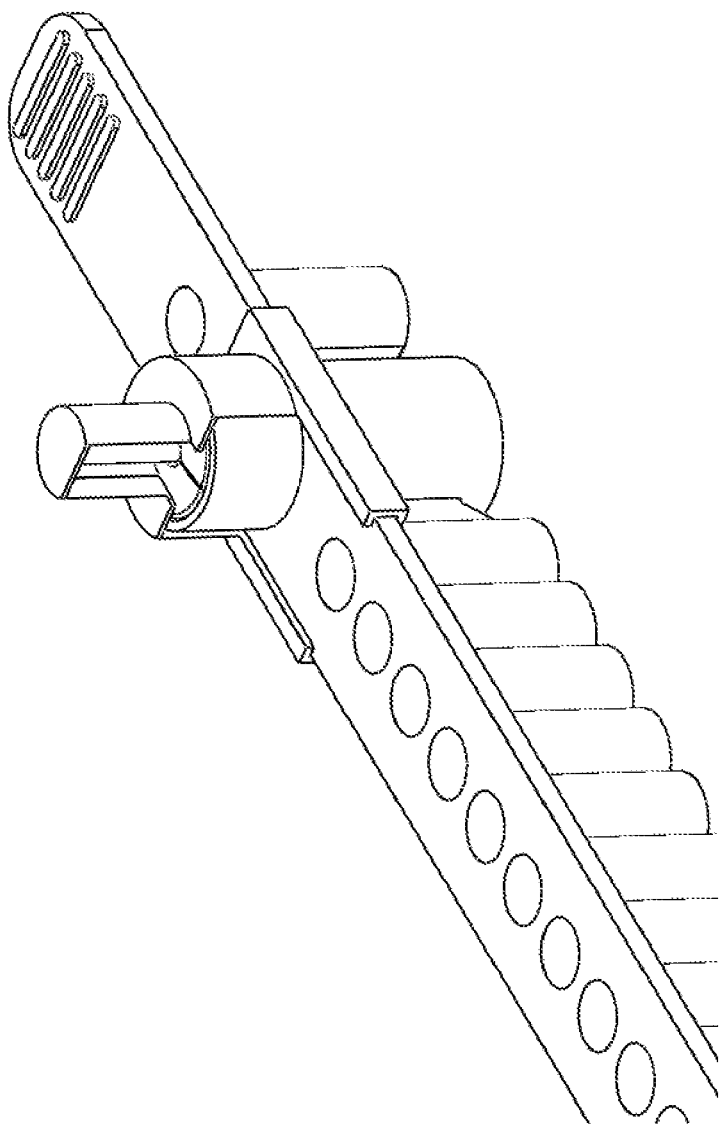
FIG. 7A illustrates another example of a probe well and a sliding cap in a close position.
Figure 7B:
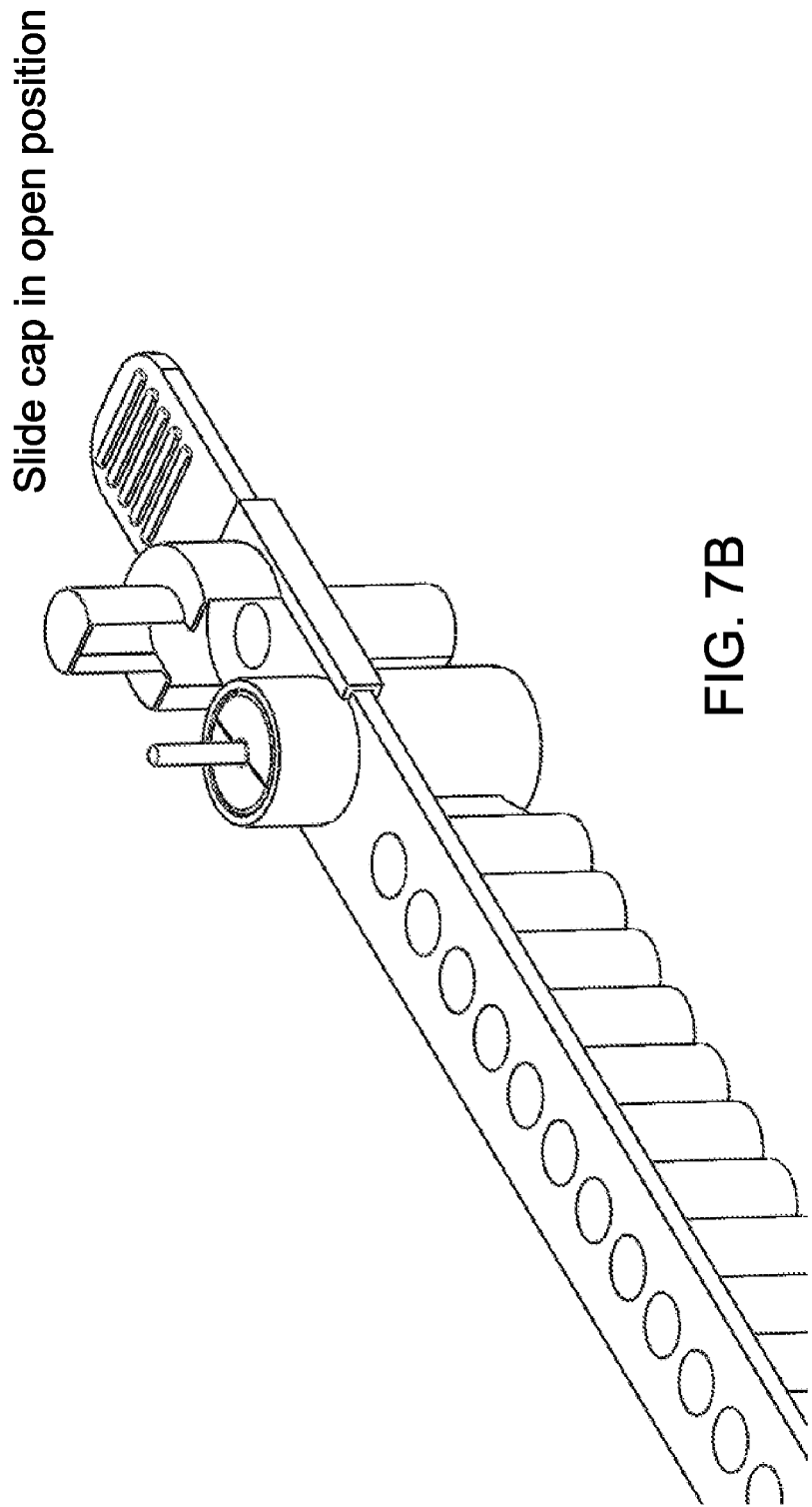
FIG. 7B illustrates another example of a probe well and a sliding cap in an open position.

Besides the hinged cap shown in FIGS. 4 and 5, the cartridge may also use a slide mechanism to open and close the cap. FIG. 6A illustrates an example of a probe well and a sliding cap in a close position, according to one embodiment of the present invention. The sliding cap may be opened as illustrated in FIG. 6B to access the probe. FIG. 7A illustrates another example of a probe well and a sliding cap in a close position, according to another embodiment of the present invention. The sliding cap may be opened as illustrated in FIG. 7B to access the probe.

Apparatus for Loading and Releasing Probe

The present invention is also directed to an apparatus for loading and releasing at least one probe having a rod-shaped portion. The apparatus comprises a groove unit and push pin. The shape of the push pin may be cylindrical, spherical, cubical, or any shape that an ordinary skill person in the art may consider suitable for the purpose. The groove unit has a groove along a vertical direction configured to hold the rod-shaped portion of the probe along the vertical direction. The push pin is configured to move along a horizontal direction. The push pin is capable of residing at a first position and a second position. When the push pin resides at the first position, a tip of the push pin is capable of pressing the rod-shaped portion of the probe against the groove. When the push pin resides at the second position, the distance between the tip of the push pin and the groove is larger than a diameter of the rod-shaped portion of the probe.

The push pin and groove is used to secure the probe between the push pin and groove so that the probe can be transferred to different locations accurately. The purpose of the apparatus is to load the probe and then dip the probe into different wells of the above-mentioned cartridge. The apparatus has means to ascend the push pin and groove and to lift the probe out of a well while the probe is loaded between the push pin and groove. The apparatus has further means to shift the push pin and groove in a horizontal plane and to shift the probe to a location on top of any wells of the cartridge. The apparatus has further means to descend the push pin and groove and to dip the bottom tip of the probe into a well while maintain a distance between the bottom tip and the inner surface of the well, so that the bottom tip is not touching any surface of the well.

FIG. 8 illustrates an example of an apparatus 800 for loading and releasing a plurality of probes 810. The apparatus 800 is able to load multiple probes 801 simultaneously, and subsequently move the probes 801 to different locations, such as different wells on cartridges. A motor 802 drives an eccentric cam 803 to move a slider in a linear motion along a shaft 805. The slider 804 is mechanically coupled to multiple push pins 810 so that the push pins are moving simultaneously in a linear motion. One end of springs 806 are fixed on a support block 807, the other end of the springs 806 is pushing the push pins 810 toward the groove unit 808. The groove unit 808 has multiple V-grooves corresponding to the push pins to load the probes 801.

Figure 9:
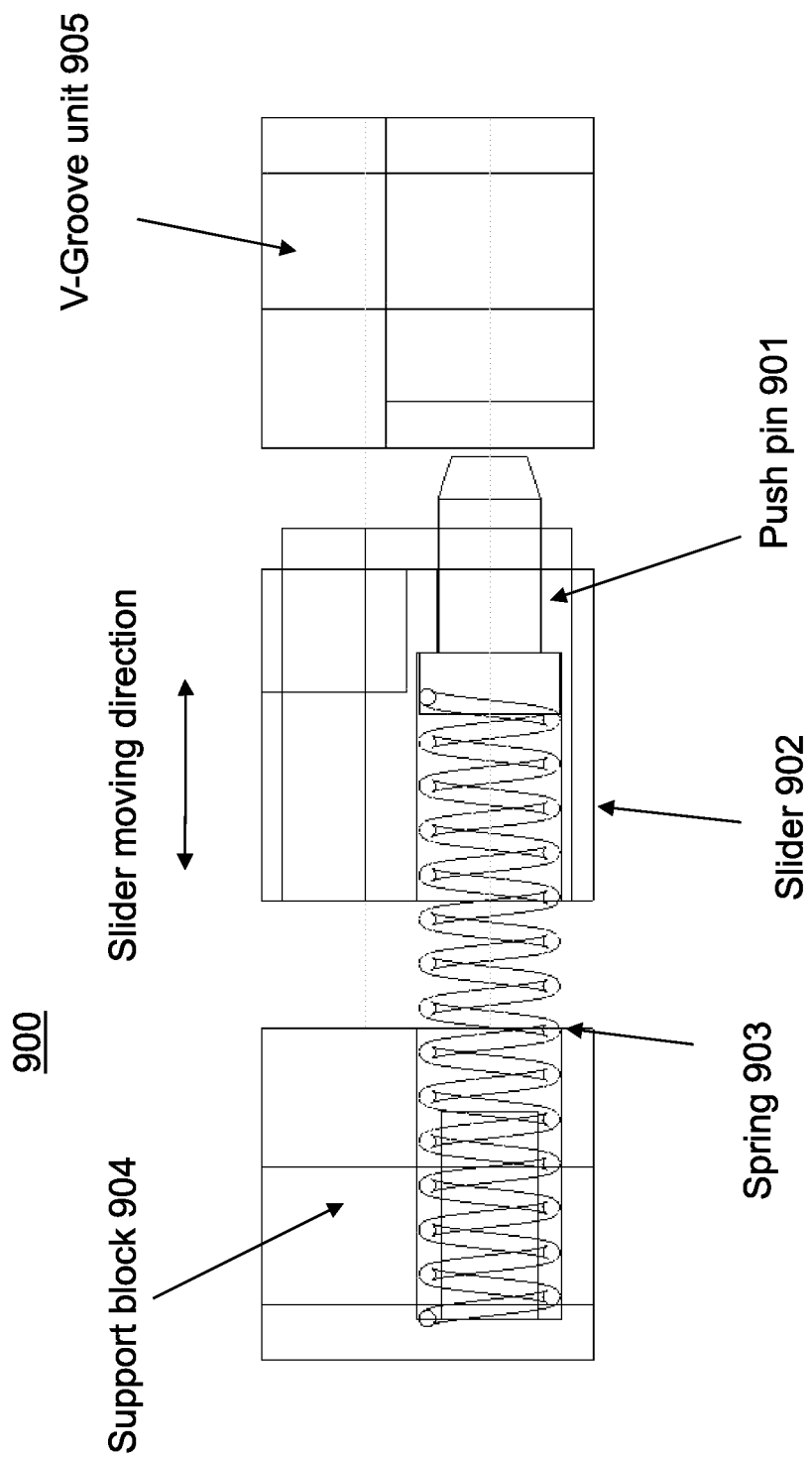
FIG. 9 is a section view of a rod loading mechanism.

FIG. 9 is a section view of the rod loading mechanism 900, according to one embodiment of the present invention. A push pin 901 is mechanically coupled to a slider 902 so that the push pin 901 and the slider 902 moves simultaneously. The slider 902 is guided by a shaft (not shown) so that the slider 902 and the push pin 901 can only move in a horizontal direction. A first end of a spring 903 is fixed on a support block 904. A second end of the spring 903 is mechanically coupled to an end of the push pin 901 providing a force to push the push pin 901 toward the groove unit 905.

Figure 10:
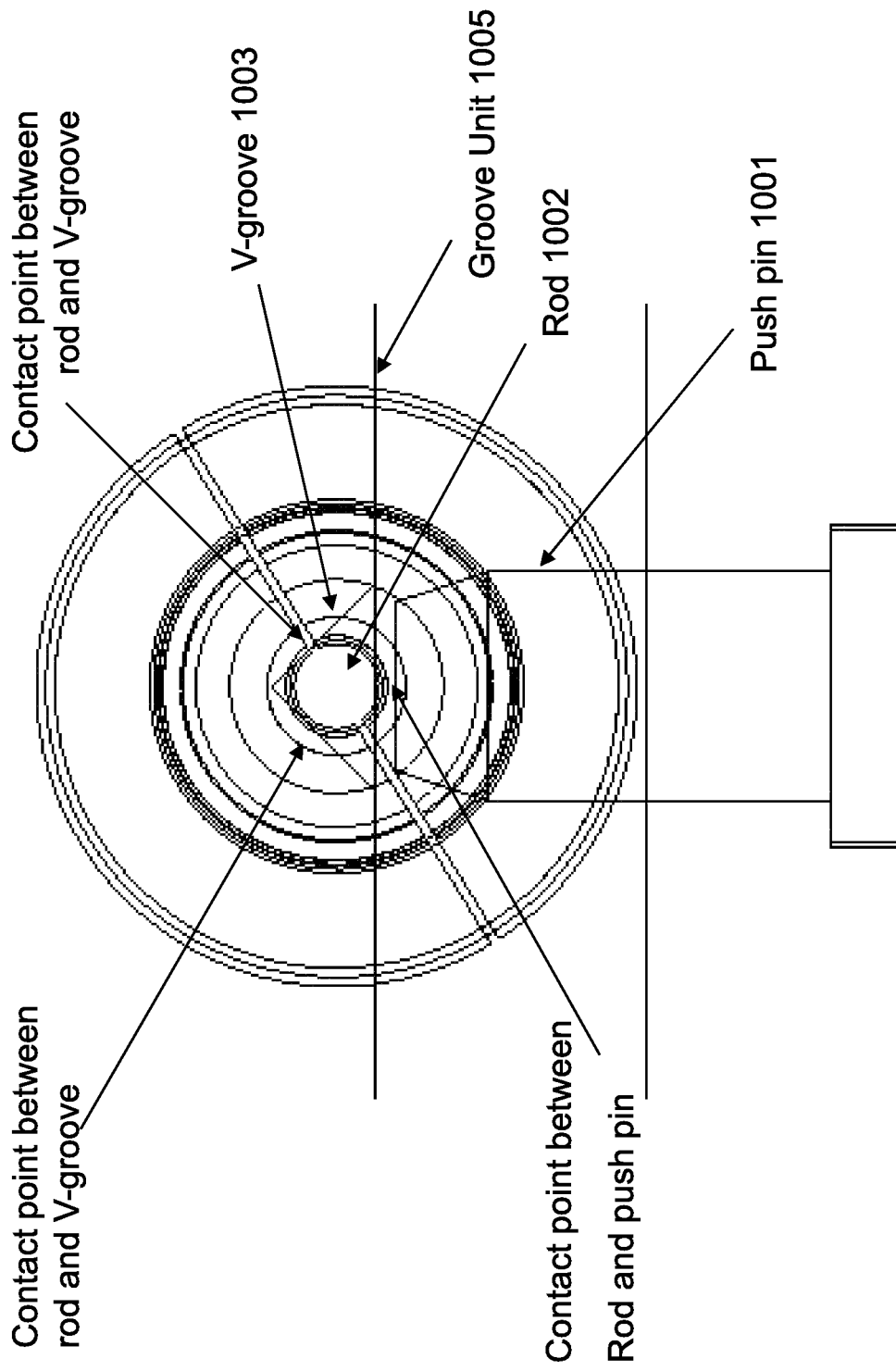
FIG. 10 illustrates a push pin pushing a rod against a V-groove.

FIG. 10 illustrates a push-pin 1001 pushing a rod 1002 against a V-groove 1003. The V-groove 1003 is on a surface of the groove unit 1005. The direction of the V-groove 1003 is along a vertical direction. The rod 1002 is a rod-shaped portion of a probe. When the rod-shaped portion is pressed against the V-groove 1003, the contacts points between the V-groove 1003 and the tip of the push pin 1001 determines the position and orientation of the probe.

Figure 11:
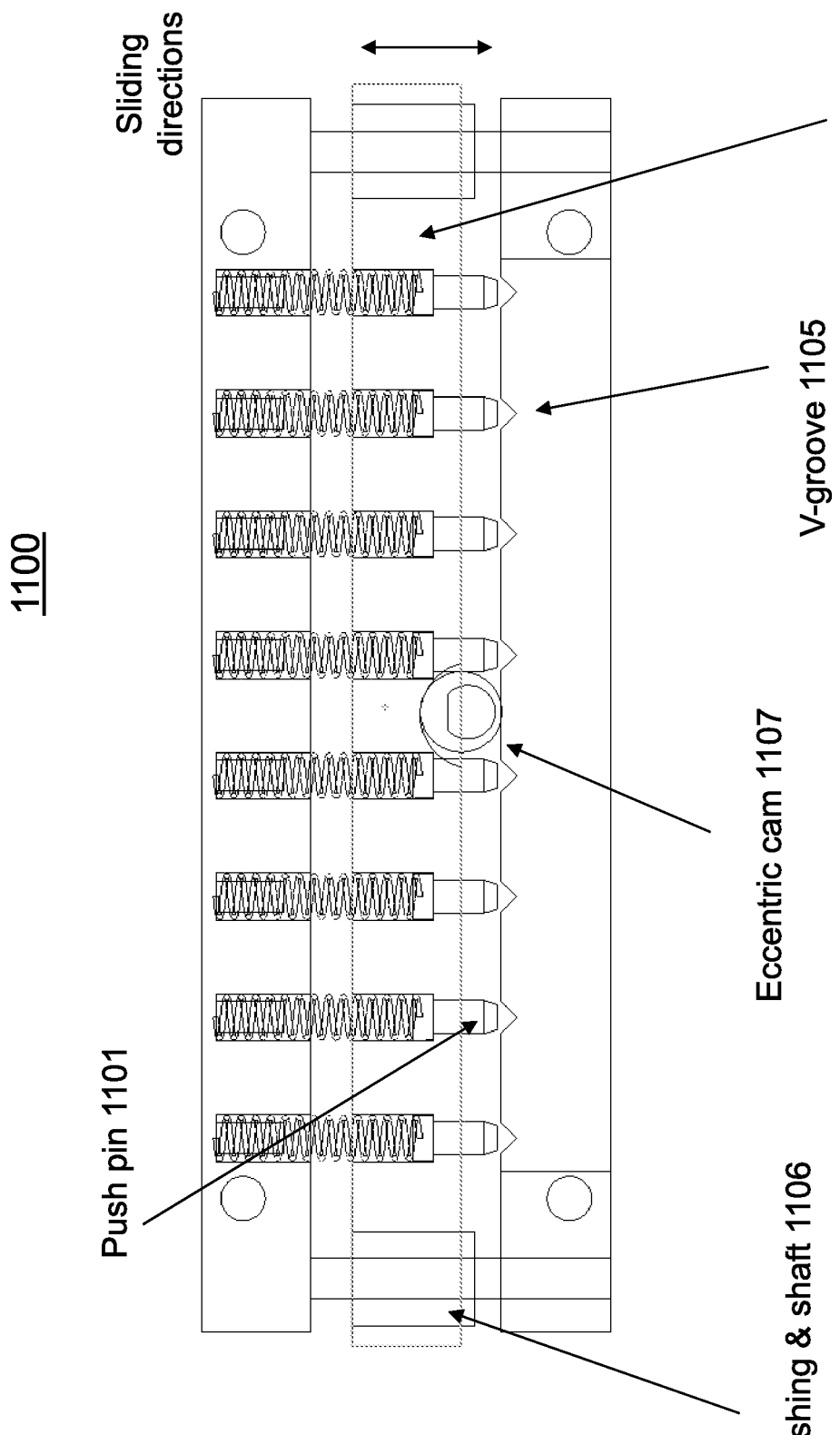
FIG. 11 is a top view of a loading mechanism.
Figure 12A:
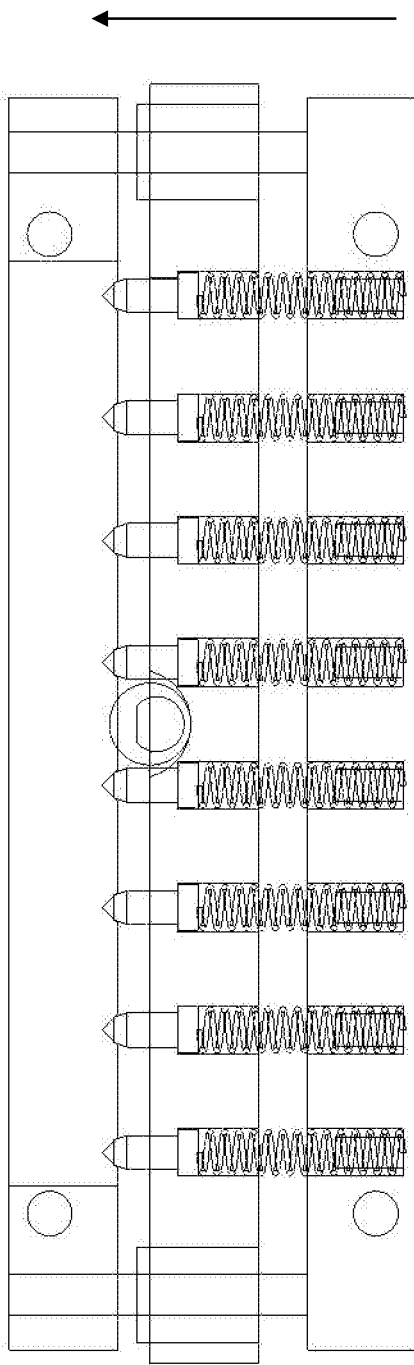
FIG. 12A shows a lock position of the eccentric cam.

FIG. 11 is a top view of a loading mechanism 1100, according to one embodiment of the present invention. The push pins are fixed inside of the holes pre-drilled in the slider 1102. The slider 1102 is guided by one or more shafts 1106 so that the slider 1102 and the push pins 1101 move in a horizontal direction simultaneously. As shown in FIGS. 9 and 11, the push pins 1101 are backed by springs to push the probes against the V-grooves 1105 on the groove unit. Eccentric cam 1107 is mechanically coupled to the slider 1102. FIG. 12A shows a lock position 1 of the eccentric cam.

Figure 12B:
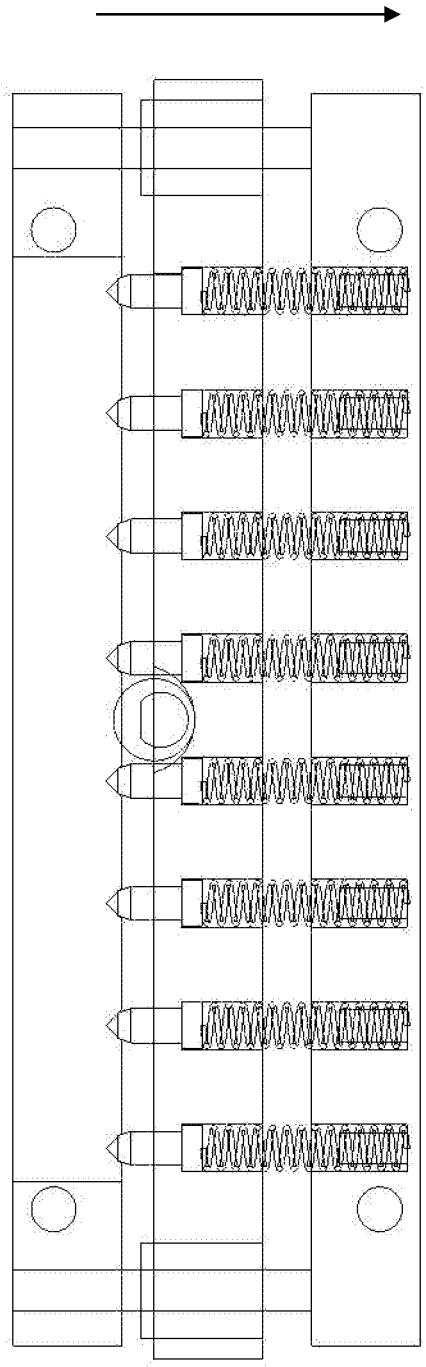
FIG. 12B shows a release position of the eccentric cam.

When the eccentric cam is in position 1 as shown, the slider is driven in a direction as indicated by the arrow in FIG. 12A. Accordingly, the push pins press the rod-shaped portion of the probe against the V-grooves. FIG. 12B shows a release position 2 of the eccentric cam. When the eccentric cam is in position 2 as shown, the slider is driven in a direction as indicated by the arrow in FIG. 12B. Accordingly, the push pins release the probe from the V-grooves.

In one embodiment, there is a provided method using the apparatus to move a probe to a plurality of locations. The method comprising (a) descending a pair of the groove unit and the push pin down in the vertical direction; (b) loading the probe between the push pin and the groove; (c) ascending the pair of the groove and the push pin up in an opposite direction of the vertical direction; (d) shifting the pair of the groove and the push pin in a horizontal plane to a location of the plurality of locations; (e) descending the pair of the groove and the push pin down in the vertical direction; and (f) repeating steps (c)-(e) at least one time. The method may use the apparatus to automatically more the probe to locations based on a pre-determined sequence.

Figure 13A:
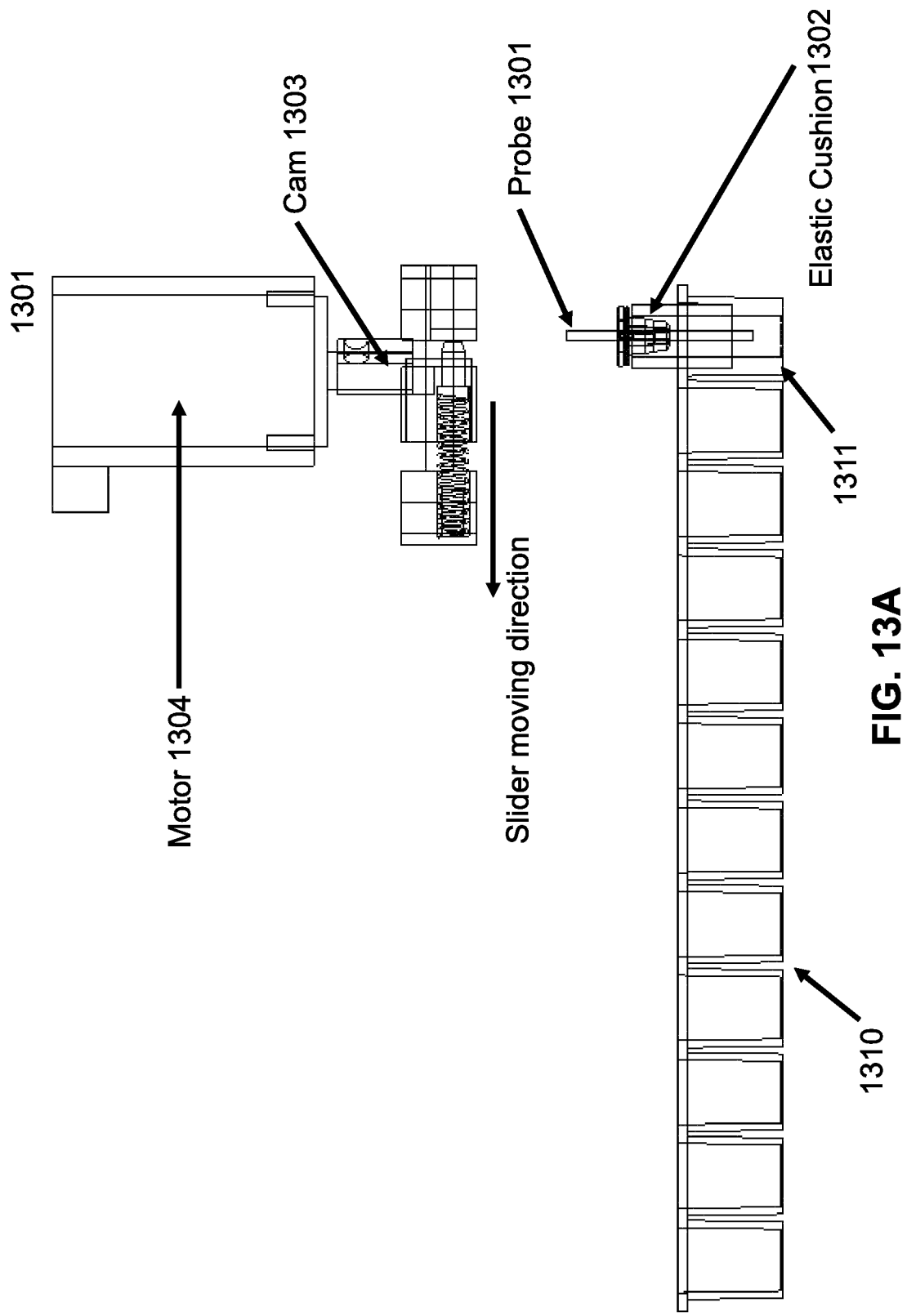
FIG. 13A illustrates an apparatus for loading a probe.
Figure 13B:
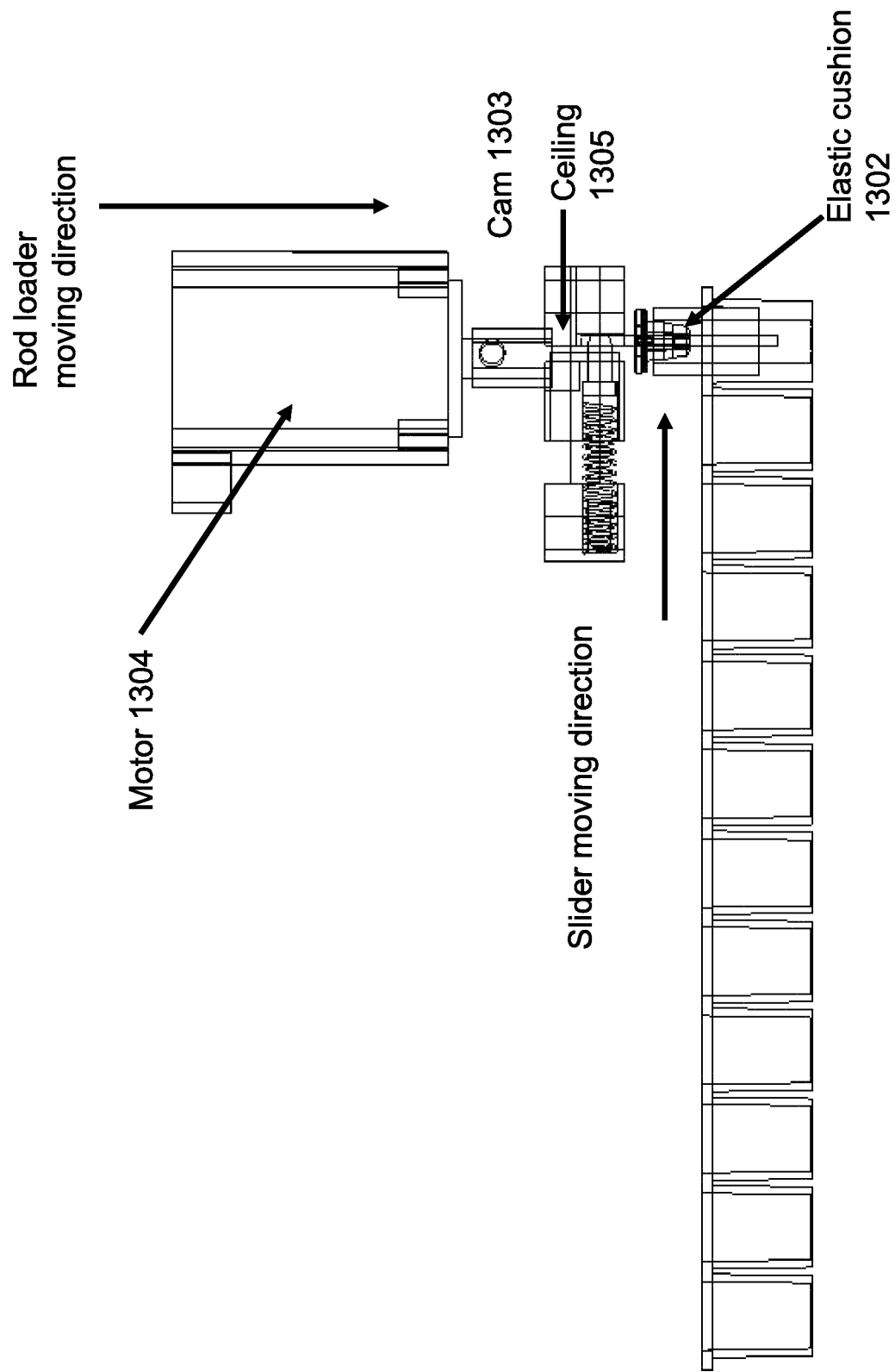
FIG. 13B illustrates an apparatus beginning to load a probe.
Figure 13C:
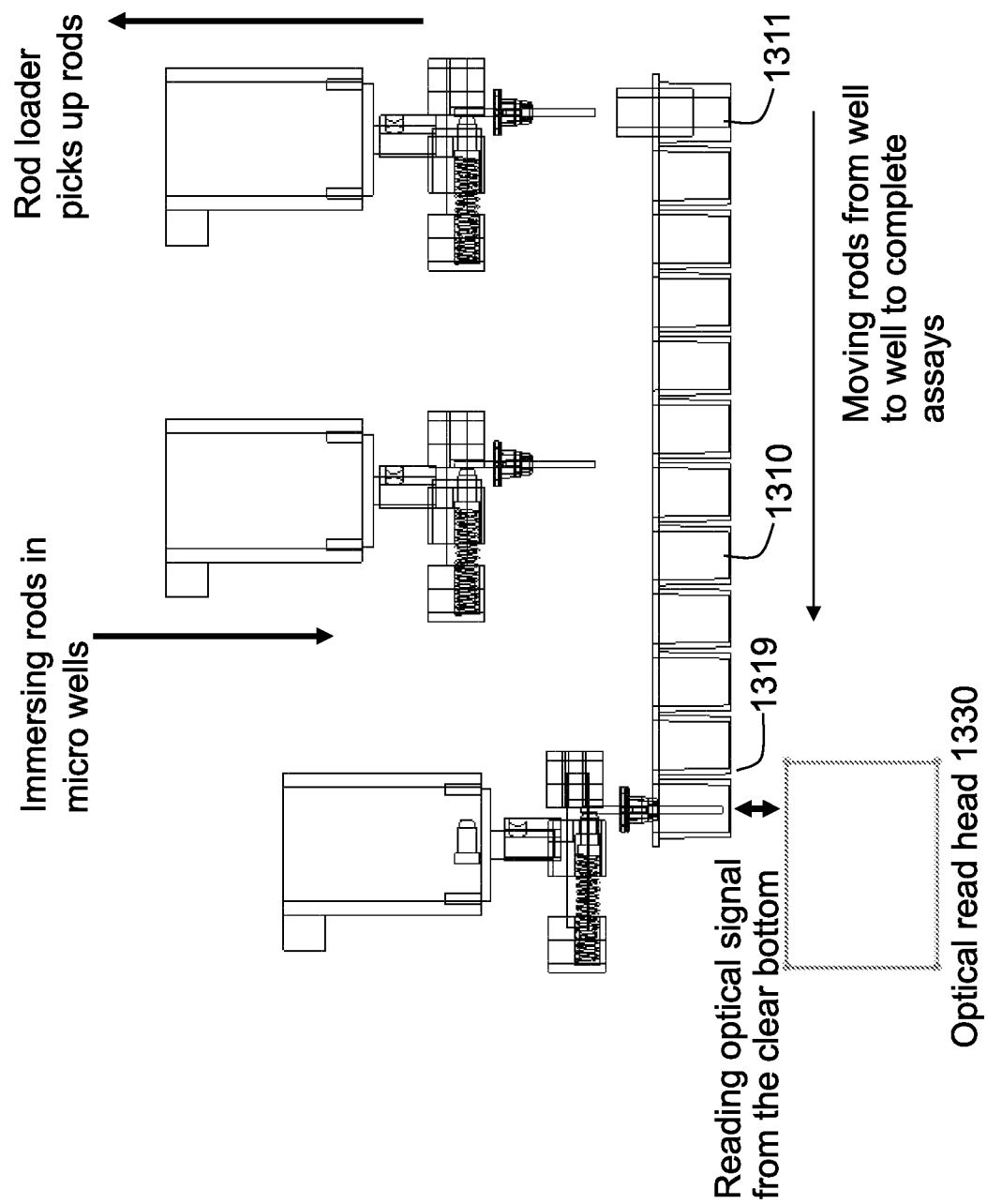
FIG. 13C illustrates an apparatus for transferring a probe to multiple wells.

FIG. 13A illustrates an apparatus 1301 for loading the probe 1302, according to one embodiment of the present invention. A probe 1301 is placed in a probe well 1311, cushioned by an elastic cushion 1302. The apparatus 1301 move the push pin and groove to a position above the probe 1301. The motor 1304 drives the eccentric cam 1303 to move the slider and push pin to a release position. Next, as shown in FIG. 13B, the apparatus 1301 moves the push pin and groove down in a vertical direction. The apparatus 1301 includes a ceiling 1305 (also referred to as top stopper). As the push pin and the groove continue to move downward and toward the probe, until a top tip of the probe touches the ceiling 1305. Thus, the ceiling 1305 ensures that a vertical position of the probe relative to the push pin and the groove is pre-determined and fixed before the push pin locks the probe. In other words, because of the ceiling 1305, the probe cannot move upward to a position where the push pin and the groove are no longer aligned with the top portion of the rod of the probe. The elastic cushion 1302 is compressed slightly so the top portion of the probe is engaged. The motor 1304 drives the eccentric cam 1303 to move the slider and push pin to a lock position. The tip of the push pin presses the rod-shaped portion of the probe against the groove to load the probe. Once the probe is loaded, the probe is moved from the probe well 1311 of the cartridge 1310. As shown in FIG. 13C, apparatus starts to move the probe from well to well to conduct the immunoassay test. Finally the probe is moved to a measurement well 1319. The measurement well may have a light transmissive bottom so that an optical read head 1330 can read optical signal emitted from the bottom tip of the probe through the light transmissive bottom.

In one embodiment, the apparatus may be utilized to load and transfer a probe to multiple wells in a cartridge, such as a cartridge shown in FIG. 3. Using a device such as a pipette, solutions in the reconstitution wells are transferred to sample well, biotin reagent well and streptavidin reagent well to reconstitute the dry reagents in these wells. The apparatus unlocks a cap of the probe well of the cartridge to an open position. Then the apparatus descends a push pin and a groove unit down in a vertical direction and loads the probe by pressing the probe against a groove on the surface of the groove unit. The apparatus ascends the groove and the push pin and shifts the groove and push pin in a horizontal plane to a location on top of the sample well, and then descends the groove and push pin to dip the bottom tip of the probe into the sample well. The sample well contains a sample solution having an analyte. The analyte reacts with the analyte-binding molecules coated on the bottom tip of the probe for a period of time to form an immunocomplex. The apparatus control the position of the probe so that the bottom tip of the probe is in the sample solution without touch any surface of the sample well. The apparatus then transfers the probe into several wash wells sequentially by similar motions of ascending, shifting and descending the push pin and groove. The apparatus transfers the probe into the biotin reagent well to allow the reaction between the immunocomplex and the biotin reagent. Afterward, the apparatus transfers the probe to several wash wells sequentially to wash away non-specifically bound materials on the probe. The apparatus further transfers the probe into the streptavidin well and several wash wells sequentially. The apparatus transfers the probe into a measurement well. The bottom tip of the probe is dipped into an aqueous solution in the measurement well. The immunocomplex formed on the bottom tip is detected by an optical signal on the bottom tip through a light transmissive bottom of the measurement well. After the signal measurement, the apparatus may transfer the probe back to the probe well, or dispose the probe to a waste bin.

Figure 14:
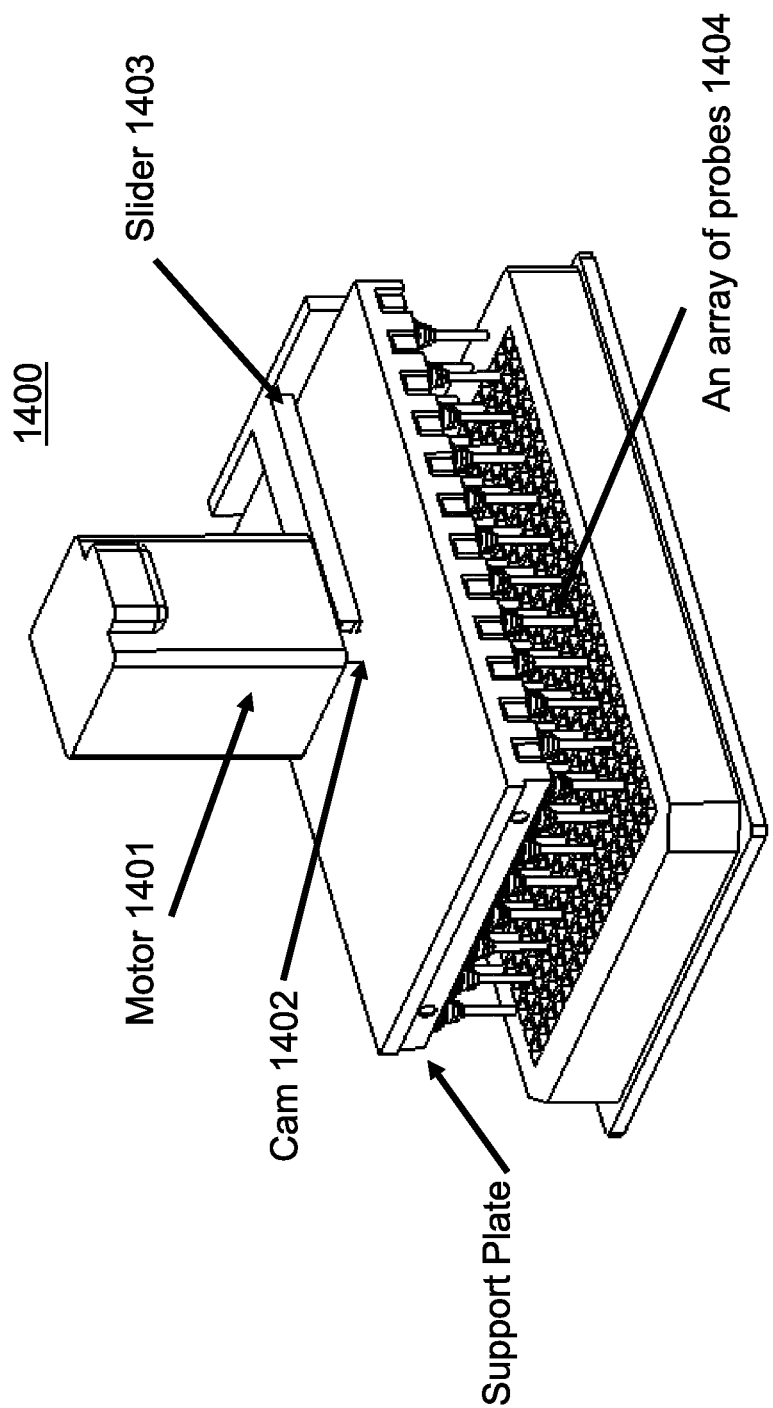
FIG. 14 shows an apparatus loading and releasing an array of probes.

In some embodiments, the apparatus can load and release 2-dimensional array of probes simultaneously. FIG. 14 shows an apparatus 1400 loading and releasing an array of 96 probes. The motor 1401 drives the eccentric cam 1402 to move the slider 1402 and a 2-dimensional array of push pins and V-grooves (not shown) to load and release an array of 96 probes 1404.

EXAMPLES

Example 1

Performing an Immunoassay Using Cartridge of the Present Invention Probe Preparation Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of murine monoclonal anti-fluorescein (Biospecific), 10 µg/ml in PBS at pH 7.4. After allowing the antibody to adsorb to the probe for 20 minutes, the probe tip was washed in PBS.

Capture antibodies to b-type naturetic peptide (BNP), obtained from HyTest, were labeled with fluorescein by standard methods. Typically, there were about 4 fluorescein substitutions per capture antibody. Anti-fluorescein coated probes were immersed in fluorescein labeled anti-BNP (5 µg/ml) for 5 minutes. followed by washing in PBS.
Cy5-Streptavidin-Crosslinked Ficoll
   Cy 5 labeling of Streptavidin is prepared according to the protocols disclosed in WO2010/101931.
Biotinylation of Anti-BNP
   Anti-BNP (Hytest Ltd.) was biotinylated by a standard method. To 1 mg anti-BNP in 1 mL of phosphate buffered saline was added 10 µL Biotin-LC-LC-NHS (Pierce Chemical) at 5 mg/ml in DMF. The mixture reacted for 1 hour at room temperature, followed by purification on a PD 10 column (GE Healthcare).
BNP Assay
Cartridge Format:
   Measurement Well: 80 µL PBS+0.05% Tween 20
   Wash Wells: 80 µL PBS+0.05% Tween 20
   Reconstitution Wells: 80 µL PBS+0.05% Tween 20

Sample Well: 25 µL BNP sample+50 µL buffer from reconstitution well

Biotin Reagent Well: 5 µL B-anti BNP (25 µg/ml)+50 µl buffer from reconstitution well Streptavidin Reagent Well: 5 µL Cy5-Streptavidin-Cross-linked Ficoll (150 µg/ml)+50 µL buffer from recon well.

Protocol:
1. Anti-BNP coated probe immersed in sample well and incubated with BNP sample mixture for 5 minutes at room temperature.
2. Probe was transferred sequentially to three wash wells, residence time 10 sec per well.
3. Probe was immersed in biotin reagent well for 2 minutes at room temperature followed by cycling through three wash wells, 10 sec each.
4. Probe was immersed in streptavidin reagent well for 1 minute at room temperature, followed by cycling through 3 wash wells, 10 sec per well.
5. Probe was positioned in measurement well
6. Fluorescence at distal tip of Probe was measured.

Results:
The Results are shown in Table 1.

TABLE 1

| BNP pg/ml | 6000 | 3000 | 1000 | 333 | 111 | 37 | Neg. |
|---|---|---|---|---|---|---|---|
| PMT Voltage (mean of duplicates) | 4.55 | 3.07 | 1.16 | 0.41 | 0.15 | 0.07 | 0.06 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method for conducting an immunoassay test, the method comprising:
   obtaining a cartridge that includes—
      a probe well in which a bottom portion of a probe is suspended, wherein the bottom portion includes a bottom tip that is coated with analyte-binding molecules,
      a cap that, when in a closed position, encloses a top portion of the probe that extends above the probe well, and
      a measurement well in which light is shone for optical reading during the immunoassay test;
   moving the cap to an open position so as to expose the top portion of the probe;
   removing the probe from the probe well and then immersing the bottom tip in a sample to be analyzed as part of the immunoassay test; and
   performing an immunoassay test.

2. The method of claim 1, wherein the cartridge further includes a sample well in which to receive the sample in which the bottom portion of the probe is immersed.

3. The method of claim 1, wherein said removing comprises:
   descending a loading mechanism with (i) a groove that is oriented in a vertical direction and (ii) a pin that is movable along a horizontal direction such that the top portion of the probe is situated within the groove,
   moving the pin along the horizontal direction in a first direction to hold the top portion of the probe in the groove, and
   ascending the loading mechanism in the vertical direction.

4. The method of claim 3, wherein said loading comprises:
   shifting the loading mechanism to a location corresponding to the measurement well,
   descending the loading mechanism in the vertical direction such that the bottom portion of the probe enters the measurement well, and
   moving the pin along the horizontal direction in a second direction opposite the first direction to release the top portion of the probe from the groove.

5. The method of claim 1, wherein the measurement well has an aqueous solution sealed therein, and wherein the method further comprises:
   removing a seal from the measurement well prior to said performing.

6. The method of claim 1, wherein the measurement well has a light-transmissive bottom that is used for optical reading of interactions between the analyte-binding molecules coated along the bottom tip of the probe and analyte molecules from the sample.

7. The method of claim 1, wherein said performing comprises:
   loading the probe into the measurement well such that the bottom portion of the probe is suspended therein.

8. A cartridge for an immunoassay test, the cartridge comprising:
   a probe well in which a bottom portion of a probe is suspended, wherein the probe has a bottom tip that is coated with analyte-binding molecules;
   a cap that is pivotably connected to the cartridge, so as to be foldable over the probe well to enclose a top portion of the probe that extends above the probe well; and
   a measurement well in which light is shone for optical reading during the immunoassay test;
   wherein over the course of the immunoassay test, the bottom tip is immersed in a sample, a reagent, and an aqueous solution before being suspended in the measurement well so as to be exposed to the light.

9. The cartridge of claim 8, further comprising:
   a sample well in which to receive the sample;
   a reagent well in which to receive the reagent; and
   at least one wash well in which to receive the aqueous solution.

10. The cartridge of claim 8,
   wherein the reagent is a dry reagent, and
   wherein the cartridge further comprises:
      a reconstitution well in which to receive a buffer for reconstituting the dry reagent.

11. The cartridge of claim 10, wherein the reagent well is one of multiple reagent wells, and wherein a different reagent is stored in each of the multiple reagent wells.

12. The cartridge of claim 11, wherein the reagent well contains antibody molecules conjugated with a first member of a binding pair, and wherein another reagent well of the multiple reagent wells contains a second member of the binding pair that is labeled with reporter molecules.

13. The cartridge of claim 12, wherein the reporter molecules are suitable for fluorescent labeling or chemiluminescent labeling.

14. The cartridge of claim 8, wherein the measurement well has a light-transmissive bottom that is used for optical reading of the probe during the immunoassay test.

15. A method for conducting an immunoassay test using the cartridge of claim 8, the method comprising:
   moving the cap so as to expose the top portion of the probe;
   removing the probe from the probe well and then immersing the bottom portion of the probe in the sample, the aqueous solution, and the reagent in succession;
   loading the probe into the measurement well such that the bottom portion of the probe is suspended therein; and
   causing the light to be shone into the measurement well for optical reading of the bottom portion of the probe.

16. The method of claim 15, wherein the measurement well has a light-transmissive bottom through which a laser is projected onto the bottom portion of the probe to excite a fluorescent label.

17. A cartridge for an immunoassay test, the cartridge comprising:
   a probe well in which a bottom portion of a probe is suspended,
      wherein the probe includes (i) a rod-shaped section and (ii) a cushioning component located in a center portion of the rod-shaped section,
      wherein a top portion of the probe extends from an upper side of the cushioning component, and
      wherein the bottom portion of the probe extends from a bottom side of the cushioning component;
   a cap that is pivotably connected to the cartridge, so as to be foldable over the probe well to enclose the top portion of the probe that extends above the probe well; and
   a measurement well in which light is shone for optical reading during the immunoassay test.

18. A cartridge for an immunoassay test, the cartridge comprising:
   a probe well in which a bottom portion of a probe is suspended;
   a cap that is pivotably connected to the cartridge, so as to be foldable over the probe well to enclose a top portion of the probe that extends above the probe well;
   a measurement well in which light is shone for optical reading during the immunoassay test;
   a first compartment that includes (i) a biotin reagent well that contains a biotinylated antibody in dry format and (ii) a streptavidin well that contains a labeled streptavidin in dry format; and
   a second compartment that includes (i) at least one reconstitution well, (ii) at least one wash well, and (iii) the measurement well;
   wherein the first and second compartments are separated by an air space to prevent liquid penetration from wells in the second compartment to wells in the first compartment.

* * * * *